(12) United States Patent
Lopes-Ferreira et al.

(10) Patent No.: US 9,309,538 B2
(45) Date of Patent: Apr. 12, 2016

(54) BETA-GLUCOSIDASE VARIANTS HAVING IMPROVED ACTIVITY, AND USES THEREOF

(75) Inventors: Nicolas Lopes-Ferreira, Croisilles (FR); Antoine Margeot, Paris (FR); Hugues Mathis, Bussy Saint Georges (FR); Laurent Fourage, Calvisson (FR)

(73) Assignees: IFP Energies Nouvelles, Rueil Malmaison (FR); PROTEUS, Nimes (FR)

( * ) Notice: Subject to any disclaimer, the term of this patent is extended or adjusted under 35 U.S.C. 154(b) by 336 days.

(21) Appl. No.: 13/063,362

(22) PCT Filed: Sep. 10, 2009

(86) PCT No.: PCT/FR2009/051701
§ 371 (c)(1),
(2), (4) Date: Mar. 10, 2011

(87) PCT Pub. No.: WO2010/029259
PCT Pub. Date: Mar. 18, 2010

(65) Prior Publication Data
US 2011/0171674 A1    Jul. 14, 2011

(30) Foreign Application Priority Data

Sep. 12, 2008 (FR) ..................................... 08 56167

(51) Int. Cl.
| | |
|---|---|
| *C12Q 1/34* | (2006.01) |
| *C12P 19/02* | (2006.01) |
| *C12P 1/00* | (2006.01) |
| *C12N 9/24* | (2006.01) |
| *C12N 1/20* | (2006.01) |
| *C12N 1/00* | (2006.01) |
| *C12N 15/00* | (2006.01) |
| *C12P 7/06* | (2006.01) |
| *C07H 21/04* | (2006.01) |
| *C12P 7/04* | (2006.01) |
| *C12P 7/10* | (2006.01) |
| *C12P 7/16* | (2006.01) |
| *C12P 19/14* | (2006.01) |
| *C12N 9/42* | (2006.01) |

(52) U.S. Cl.
CPC ................ *C12P 7/04* (2013.01); *C12N 9/2445* (2013.01); *C12P 7/10* (2013.01); *C12P 7/16* (2013.01); *C12P 19/02* (2013.01); *C12P 19/14* (2013.01); *C12Y 302/01021* (2013.01); *Y02E 50/10* (2013.01); *Y02E 50/16* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 2004/0253702 A1 | 12/2004 | Fidantsef et al. | |
| 2007/0077630 A1 | 4/2007 | Harris et al. | |
| 2009/0280105 A1* | 11/2009 | Gusakov et al. | ........... 424/94.61 |

FOREIGN PATENT DOCUMENTS

| | | | |
|---|---|---|---|
| KR | 2003-0046570 | * | 6/2003 |
| WO | 2005-074647 | | 8/2005 |

OTHER PUBLICATIONS

Barrera-Islas et al., "Characterization of a β-Glucosidase Produced by a High-Specific Growth-Rate Mutant of Cellulomonas flavigena" (2007) Current Microbiology, vol. 54, No. 4: pp. 266-270.
Database, Geneseq [Online] Jun. 17, 2004, "Trichoderma sp. C-4 beta-glucosidase, SEQ ID 2." XP002510451.
Database, UniProt [Online] May 20, 2008, "SubName: Full=Predicted CDS Pa_3_590;" XP002510452.
Database, UniProt [Online] May 15, 2007, "SubName: Full=Putative uncharacterized protein;" XP002510453.
Database, UniProt [Online] Mar. 21, 2006, "SubName: Full=Putative uncharacterized protein;" XP002510454.

* cited by examiner

*Primary Examiner* — Iqbal H Chowdhury
(74) *Attorney, Agent, or Firm* — McDonnell Boehnen Hulbert & Berghoff

(57) ABSTRACT

The present invention relates to the expression and optimization of enzymes involved in lignocellulosic biomass decomposition. The present invention relates more particularly to beta-glucosidase variants comprising at least one modification among the amino acids located at positions 225, 238, 240 and 241, according to the numbering in SEQ ID No. 2 of *Trichoderma reesei* beta-glucosidase, and also relates to the use of said variants having improved effectiveness in methods for cellulose decomposition and biofuel production.

11 Claims, 1 Drawing Sheet

SEQUENCE LISTING

```
<160> NUMBER OF SEQ ID NOS: 18

<210> SEQ ID NO 1
<211> LENGTH: 2235
<212> TYPE: DNA
<213> ORGANISM: Trichoderma reesei

<400> SEQUENCE: 1
atgcgttacc gaacagcagc tgcgctggca cttgccactg ggcctttgc tagggcagac      60 agtcactcaa catcggggc ctcggctgag gcagttgtac ctcctgcagg gactccatgg     120
ggaaccgcgt acgacaaggc gaaggccgca ttggcaaagc tcaatctcca agataaggtc     180
ggcatcgtga gcggtgtcgg ctggaacggc ggtccttgcg ttggaaacac atctccggcc     240
tccaagatca gctatccatc gctatgcctt caagacggac ccctcggtgt tcgatactcg     300
acaggcagca cagcctttac gccgggcgtt caagcggcct cgacgtggga tgtcaatttg     360
atccgcgaac gtggacagtt catcggtgag gaggtgaagg cctcggggat tcatgtcata     420
cttggtcctg tggctgggcc gctgggaaag actccgcagg gcggtcgcaa ctgggagggc     480
ttcggtgtcg atccatatct cacgggcatt gccatgggtc aaaccatcaa cggcatccag     540
tcggtaggcg tgcaggcgac agcgaagcac tatatcctca acgagcagga gctcaatcga     600
gaaaccattt cgagcaaccc agatgaccga actctccatg agctgtatac ttggccattt     660
gccgacgcgg ttcaggccaa tgtcgcttct gtcatgtgct cgtacaacaa ggtcaatacc     720
acctgggcct gcgaggatca gtacacgctg cagactgtgc tgaaagacca gctggggttc     780
ccaggctatg tcatgacgga ctggaacgca cagcacacga ctgtccaaag cgcgaattct     840
gggcttgaca tgtcaatgcc tggcacagac ttcaacggta acaatcggct ctggggtcca     900
gctctcacca atgcggtaaa tagcaatcag gtccccacga gcagagtcga cgatatggtg     960
actcgtatcc tcgccgcatg gtacttgaca ggccaggacc aggcaggcta tccgtcgttc    1020
aacatcagca gaaatgttca aggaaaccac aagaccaatg tcagggcaat tgccagggac    1080
ggcatcgttc tgctcaagaa tgacgccaac atcctgccgc tcaagaagcc cgctagcatt    1140
gccgtcgttg gatctgccgc aatcattggt aaccacgcca gaaactcgcc ctcgtgcaac    1200
gacaaaggct gcgacgacgg ggccttgggc atgggttggg gttccggcgc cgtcaactat    1260
ccgtacttcg tcgcgcccta cgatgccatc aataccagag cgtcttcgca gggcacccag    1320
gttaccttga gcaacaccga caacacgtcc tcaggcgcat ctgcagcaag aggaaaggac    1380
gtcgccatcg tcttcatcac cgccgactcg ggtgaaggct acatcaccgt ggagggcaac    1440
gcgggcgatc gcaacaacct ggatccgtgg cacaacggca atgccctggt ccaggcggtg    1500
gccggtgcca acagcaacgt cattgttgtt gtccactccg ttggcgccat cattctggag    1560
cagattcttg ctcttccgca ggtcaaggcc gttgtctggg cgggtcttcc ttctcaggag    1620
agcggcaatg cgctcgtcga cgtgctgtgg ggagatgtca gcccttctgg caagctggtg    1680
tacaccattg cgaagagccc caatgactat aacactcgca tcgtttccgg cggcagtgac    1740
```

```
agcttcagcg agggactgtt catcgactat aagcacttcg acgacgccaa tatcacgccg    1800
cggtacgagt tcggctatgg actgtcttac accaagttca actactcacg cctctccgtc    1860
ttgtcgaccg ccaagtctgg tcctgcgact ggggccgttg tgccgggagg cccgagtgat    1920
ctgttccaga atgtcgcgac agtcaccgtt gacatcgcaa actctggcca agtgactggt    1980
gccgaggtag cccagctgta catcacctac ccatcttcag cacccaggac ccctccgaag    2040
cagctgcgag gctttgccaa gctgaacctc acgcctggtc agagcggaac agcaacgttc    2100
aacatccgac gacgagatct cagctactgg gacacggctt cgcagaaatg ggtggtgccg    2160
tcggggtcgt ttggcatcag cgtgggagcg agcagccggg atatcaggct gacgagcact    2220
ctgtcggtag cgtag                                                     2235
```

<210> SEQ ID NO 2
<211> LENGTH: 744
<212> TYPE: PRT
<213> ORGANISM: Trichoderma reesei

<400> SEQUENCE: 2

```
Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
            20                  25                  30

Val Pro Pro Ala Gly Thr Pro Trp Gly Thr Ala Tyr Asp Lys Ala Lys
        35                  40                  45

Ala Ala Leu Ala Lys Leu Asn Leu Gln Asp Lys Val Gly Ile Val Ser
    50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
    130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
```

-continued

```
              275                 280                 285
Thr Asp Phe Asn Gly Asn Asn Arg Leu Trp Gly Pro Ala Leu Thr Asn
290                 295                 300
Ala Val Asn Ser Asn Gln Val Pro Thr Ser Arg Val Asp Asp Met Val
305                 310                 315                 320
Thr Arg Ile Leu Ala Ala Trp Tyr Leu Thr Gly Gln Asp Gln Ala Gly
                325                 330                 335
Tyr Pro Ser Phe Asn Ile Ser Arg Asn Val Gln Gly Asn His Lys Thr
                340                 345                 350
Asn Val Arg Ala Ile Ala Arg Asp Gly Ile Val Leu Leu Lys Asn Asp
                355                 360                 365
Ala Asn Ile Leu Pro Leu Lys Lys Pro Ala Ser Ile Ala Val Val Gly
370                 375                 380
Ser Ala Ala Ile Ile Gly Asn His Ala Arg Asn Ser Pro Ser Cys Asn
385                 390                 395                 400
Asp Lys Gly Cys Asp Asp Gly Ala Leu Gly Met Gly Trp Gly Ser Gly
                405                 410                 415
Ala Val Asn Tyr Pro Tyr Phe Val Ala Pro Tyr Asp Ala Ile Asn Thr
                420                 425                 430
Arg Ala Ser Ser Gln Gly Thr Gln Val Thr Leu Ser Asn Thr Asp Asn
                435                 440                 445
Thr Ser Ser Gly Ala Ser Ala Ala Arg Gly Lys Asp Val Ala Ile Val
450                 455                 460
Phe Ile Thr Ala Asp Ser Gly Glu Gly Tyr Ile Thr Val Glu Gly Asn
465                 470                 475                 480
Ala Gly Asp Arg Asn Asn Leu Asp Pro Trp His Asn Gly Asn Ala Leu
                485                 490                 495
Val Gln Ala Val Ala Gly Ala Asn Ser Asn Val Ile Val Val Val His
                500                 505                 510
Ser Val Gly Ala Ile Ile Leu Glu Gln Ile Leu Ala Leu Pro Gln Val
                515                 520                 525
Lys Ala Val Val Trp Ala Gly Leu Pro Ser Gln Glu Ser Gly Asn Ala
530                 535                 540
Leu Val Asp Val Leu Trp Gly Asp Val Ser Pro Ser Gly Lys Leu Val
545                 550                 555                 560
Tyr Thr Ile Ala Lys Ser Pro Asn Asp Tyr Asn Thr Arg Ile Val Ser
                565                 570                 575
Gly Gly Ser Asp Ser Phe Ser Glu Gly Leu Phe Ile Asp Tyr Lys His
                580                 585                 590
Phe Asp Asp Ala Asn Ile Thr Pro Arg Tyr Glu Phe Gly Tyr Gly Leu
                595                 600                 605
Ser Tyr Thr Lys Phe Asn Tyr Ser Arg Leu Ser Val Leu Ser Thr Ala
                610                 615                 620
Lys Ser Gly Pro Ala Thr Gly Ala Val Val Pro Gly Gly Pro Ser Asp
625                 630                 635                 640
Leu Phe Gln Asn Val Ala Thr Val Thr Val Asp Ile Ala Asn Ser Gly
                645                 650                 655
Gln Val Thr Gly Ala Glu Val Ala Gln Leu Tyr Ile Thr Tyr Pro Ser
                660                 665                 670
Ser Ala Pro Arg Thr Pro Pro Lys Gln Leu Arg Gly Phe Ala Lys Leu
                675                 680                 685
Asn Leu Thr Pro Gly Gln Ser Gly Thr Ala Thr Phe Asn Ile Arg Arg
690                 695                 700
```

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
            725                 730                 735

Leu Thr Ser Thr Leu Ser Val Ala
            740

<210> SEQ ID NO 3
<211> LENGTH: 2235
<212> TYPE: DNA
<213> ORGANISM: artificial
<220> FEATURE:
<223> OTHER INFORMATION: clone 10H7

<400> SEQUENCE: 3

| | |
|---|---:|
| atgcgttacc gaacagcagc tgcgctggca cttgccactg ggccctttgc tagggcagac | 60 |
| agtcactcaa catcggggc ctcggctgag gcagttgtac ctcctgcagg gactccatgg | 120 |
| ggaaccgcgt acgacaaggc gaaggccgca ttggcaaagc tcaatctcca agataaggtc | 180 |
| ggcatcgtga gcggtgtcgg ctggaacggc ggtccttgcg ttggaaacac atctccggcc | 240 |
| tccaagatca gctatccatc gctatgcctt caagacggac ccctcggtat ccgattcggc | 300 |
| acaggcagca cagcctttac gccgggcgtt caagcggcct cgacgtggga taccgagttg | 360 |
| atgcgccagc gtggagagta cctgggtgcc gaggccaagg ctgcgggat catgtcctg | 420 |
| cttggtcctg tggctggggc cctgggaaag atcccgcacg gcggtcgcaa ctgggagggc | 480 |
| ttcggtaccg atccatatct cgccggcatt gccatggccg agacaatcga gggcctgcag | 540 |
| tcggccggcg tgcaggcgtg cgcgaagcac tatatcgtca acgagcagga gctcaatcga | 600 |
| gaaaccattt cgagcgacgt cgatgaccga actatgcatg agctgtatct gtggccattt | 660 |
| gccgacgcgg ttcacgccaa tgtcgcttct gtcatgtgct cgtacaacaa ggtcaatacc | 720 |
| acctgggcct gcgaggatca gtacacgctg cagactgtgc tgaaagacca gctggggttc | 780 |
| ccaggctatg tcatgacgga ctggaacgca cagcacacga ctgtccaaag cgcgaattct | 840 |
| gggcttgaca tgtcaatgcc tggcacagac ttcaacggta caatcggct ctggggtcca | 900 |
| gctctcacca atgcggtaaa tagcaatcag gtccccacga gcagagtcga cgatatggtg | 960 |
| actcgtatcc tcgccgcatg gtacttgaca ggccaggacc aggcaggcta tccgtcgttc | 1020 |
| aacatcagca gaaatgttca aggaaaccac aagaccaatg tcagggcaat tgccagggac | 1080 |
| ggcatcgttc tgctcaagaa tgacgccaac atcctgccgc tcaagaagcc cgctagcatt | 1140 |
| gccgtcgttg gatctgccgc aatcattggt aaccacgcca gaaactcgcc ctcgtgcaac | 1200 |
| gacaaaggct gcgacgacgg ggccttgggc atgggttggg gttccggcgc cgtcaactat | 1260 |
| ccgtacttcg tcgcgcccta cgatgccatc aataccgag cgtcttcgca gggcacccag | 1320 |
| gttaccttga gcaacaccga caacacgtcc tcaggcgcat ctgcagcaag aggaaaggac | 1380 |
| gtcgccatcg tcttcatcac cgccgactcg ggtgaaggct acatcaccgt ggagggcaac | 1440 |
| gcgggcgatc gcaacaacct ggatccgtgg cacaacggca atgccctggt ccaggcggtg | 1500 |
| gccggtgcca acagcaacgt cattgttgtt gtccactccg ttggcgccat cattctggag | 1560 |
| cagattcttg ctcttccgca ggtcaaggcc gttgtctggg cgggtcttcc ttctcaggag | 1620 |
| agcggcaatg cgctcgtcga cgtgctgtgg ggagatgtca gcccttctgg caagctggtg | 1680 |
| tacaccattg cgaagagccc caatgactat aacactcgca tcgtttccgg cggcagtgac | 1740 |
| agcttcagcg agggactgtt catcgactat aagcacttcg acgacgccaa tatcacgccg | 1800 |

```
cggtacgagt tcggctatgg actgtcttac accaagttca actactcacg cctctccgtc   1860
ttgtcgaccg ccaagtctgg tcctgcgact ggggccgttg tgccgggagg cccgagtgat   1920
ctgttccaga atgtcgcgac agtcaccgtt gacatcgcaa actctggcca agtgactggt   1980
gccgaggtag cccagctgta catcacctac ccatcttcag cacccaggac ccctccgaag   2040
cagctgcgag gctttgccaa gctgaacctc acgcctggtc agagcggaac agcaacgttc   2100
aacatccgac gacgagatct cagctactgg gacacggctt cgcagaaatg ggtggtgccg   2160
tcggggtcgt ttggcatcag cgtgggagcg agcagccggg atatcaggct gacgagcact   2220
ctgtcggtag cgtag                                                    2235
```

<210> SEQ ID NO 4
<211> LENGTH: 744
<212> TYPE: PRT
<213> ORGANISM: artificial
<220> FEATURE:
<223> OTHER INFORMATION: clone 10H7

<400> SEQUENCE: 4

```
Met Arg Tyr Arg Thr Ala Ala Leu Ala Leu Ala Thr Gly Pro Phe
1               5                  10                  15

Ala Arg Ala Asp Ser His Ser Thr Ser Gly Ala Ser Ala Glu Ala Val
            20                  25                  30

Val Pro Pro Ala Gly Thr Pro Trp Gly Thr Ala Tyr Asp Lys Ala Lys
        35                  40                  45

Ala Ala Leu Ala Lys Leu Asn Leu Gln Asp Lys Val Gly Ile Val Ser
    50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Ile Arg Phe Gly Thr Gly Ser Thr Ala Phe Thr Pro Gly Val Gln Ala
            100                 105                 110

Ala Ser Thr Trp Asp Thr Glu Leu Met Arg Gln Arg Gly Glu Tyr Leu
        115                 120                 125

Gly Ala Glu Ala Lys Gly Cys Gly Ile His Val Leu Leu Gly Pro Val
    130                 135                 140

Ala Gly Ala Leu Gly Lys Ile Pro His Gly Gly Arg Asn Trp Glu Gly
145                 150                 155                 160

Phe Gly Thr Asp Pro Tyr Leu Ala Gly Ile Ala Met Ala Glu Thr Ile
                165                 170                 175

Glu Gly Leu Gln Ser Ala Gly Val Gln Ala Cys Ala Lys His Tyr Ile
            180                 185                 190

Val Asn Glu Gln Glu Leu Asn Arg Glu Thr Ile Ser Ser Asp Val Asp
        195                 200                 205

Asp Arg Thr Met His Glu Leu Tyr Leu Trp Pro Phe Ala Asp Ala Val
    210                 215                 220

His Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
```

```
              275                 280                 285
Thr Asp Phe Asn Gly Asn Asn Arg Leu Trp Gly Pro Ala Leu Thr Asn
290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
            325                 330                 335

Tyr Pro Ser Phe Asn Ile Ser Arg Asn Val Gln Gly Asn His Lys Thr
                340                 345                 350

Asn Val Arg Ala Ile Ala Arg Asp Gly Ile Val Leu Leu Lys Asn Asp
            355                 360                 365

Ala Asn Ile Leu Pro Leu Lys Lys Pro Ala Ser Ile Ala Val Val Gly
370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
            435                 440                 445

Thr Ser Ser Gly Ala Ser Ala Ala Arg Gly Lys Asp Val Ala Ile Val
450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val His Val
            500                 505                 510

Ser Val Gly Ala Ile Ile Leu Glu Gln Ile Leu Ala Leu Pro Gln Val
            515                 520                 525

Lys Ala Val Val Trp Ala Gly Leu Pro Ser Gln Glu Ser Gly Asn Ala
530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
            595                 600                 605

Ser Tyr Thr Lys Phe Asn Tyr Ser Arg Leu Ser Val Leu Ser Thr Ala
            610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Lys Gln Leu Arg Gly Phe Ala Lys Leu
            675                 680                 685

Asn Leu Thr Pro Gly Gln Ser Gly Thr Ala Thr Phe Asn Ile Arg Arg
690                 695                 700
```

Arg Asp Leu Ser Tyr Trp Asp Thr Ala Ser Gln Lys Trp Val Pro
705                 710                 715                 720

Ser Gly Ser Phe Gly Ile Ser Val Gly Ala Ser Ser Arg Asp Ile Arg
            725                 730                 735

Leu Thr Ser Thr Leu Ser Val Ala
        740

<210> SEQ ID NO 5
<211> LENGTH: 2232
<212> TYPE: DNA
<213> ORGANISM: artificial
<220> FEATURE:
<223> OTHER INFORMATION: clone 59B8

<400> SEQUENCE: 5

| | | | | | |
|---|---|---|---|---|---|
| atgcgttacc | gaacagcagc | tgcgctggca | cttgccactg | ggccctttgc | tagggcagac | 60 |
| agtcactcaa | catcggggc | ctcggctgag | gcagttgtac | ctcctgcagg | gactccatgg | 120 |
| ggaaccgcgt | acgacaaggc | gaaggccgca | ttggcaaagc | tcaatctcca | agataaggtc | 180 |
| ggcatcgtga | gcggtgtcgg | ctggaacggc | ggtccttgcg | ttggaaacac | atctccggcc | 240 |
| tccaagatca | gctatccatc | gctatgcctt | caagacggac | ccctcggtat | ccgattcggc | 300 |
| acaggcagca | cagcctttac | gccgggcgtt | caagcggcct | cgacgtggga | taccgagttg | 360 |
| atgcgccagc | gtggagagta | cctgggtgcc | gaggccaagg | gctgcgggat | tcatgtcctg | 420 |
| cttggtcctg | tggctggggc | cctgggaaag | atcccgcacg | gcggtcgcaa | ctgggagggc | 480 |
| ttcggtaccg | atccatatct | cgccggcatt | gccatggccg | agacaatcga | gggcctgcag | 540 |
| tcggccggcg | tgcaggcgtg | cgcgaagcac | tatatcgtca | acgagcagga | gctcaatcga | 600 |
| gaaaccattt | cgagcgacgt | cgatgaccga | actatgcatg | agctgtatct | gtggccattt | 660 |
| gccgacgcgg | ttcacgccaa | tgtcgcttct | gtcatgtgct | cgtacaacaa | ggtcaatacc | 720 |
| acctgggcct | gcgaggatca | gtacacgctg | cagactgtgc | tgaaagacca | gctgggttc | 780 |
| ccaggctatg | tcatgacgga | ctggaacgca | cagcacacga | ctgtccaaag | cgcgaattct | 840 |
| gggcttgaca | tgtcaatgcc | tggcacagac | ttcaacggta | caatcggct | tggggtcca | 900 |
| gctctcacca | atgcggtaaa | tagcaatcag | gtccccacga | gcagagtcga | cgatatggtg | 960 |
| actcgtatcc | tcgccgcatg | gtacttgaca | ggccaggacc | aggcaggcta | tccgtcgttc | 1020 |
| aacatcagca | gaaatgttca | aggaaaccac | aagaccaatg | tcagggcaat | tgccagggac | 1080 |
| ggcatcgttc | tgctcaagaa | tgacgccaac | atcctgccgc | tcaagaagcc | cgctagcatt | 1140 |
| gccgtcgttg | gatctgccgc | aatcattggt | aaccacgcca | gaaactcgcc | tcgtgcaac | 1200 |
| gacaaaggct | gcgacgacgg | ggccttgggc | atgggttggg | gttccggcgc | cgtcaactat | 1260 |
| ccgtacttcg | tcgcgcccta | cgatgccctc | aagaccagag | cgtcttcgca | gggcacccag | 1320 |
| gttaccttga | gcaacaccga | caacacgtcc | tcaggcgcat | ctgcagcaag | aggaaaggac | 1380 |
| gtcgccatcg | tcttcatcac | cgccgactcg | ggtgaaggct | acatcaccgt | ggagggcaac | 1440 |
| gcgggcgatc | gcaacaacct | ggatccgtgg | cacaacggca | atgccctggt | ccaggcggtg | 1500 |
| gccggtgcca | acagcaacgt | cattgttgtt | gtccactccg | ttggcgccat | cattctggag | 1560 |
| cagattcttg | ctcttccgca | ggtcaaggcc | gttgtctggg | cgggtcttcc | ttctcaggag | 1620 |
| agcggcaatg | cgctcgtcga | cgtgctgtgg | ggagatgtca | gcccttctgg | caagctggtg | 1680 |
| tacaccattg | cgaagagccc | caatgactat | aacactcgca | tcgtttccgg | cggcagtgac | 1740 |
| agcttcagcg | agggactgtt | catcgactat | aagcacttcg | acgacgccaa | gatcgagccg | 1800 |

```
cggtacgagt tcggcttcgg actgtcttac accgagttca cctacgccga cctctccgtc    1860
acctcgaccg tcaccgccgg tcctgcgagc ggggagacaa tcccgggagg cgccgccgat    1920
ctgtgggaga cagtcgcgac agtcaccgcc agcatcacca actctggcga ggtggagggt    1980
gccgaggtag cccagctgta catcaccctg ccatctgccg cacccagcac ccctccgaag    2040
cagctgcgag gctttgccaa gctgaagctc gagcctggtg ccagcggagt cgcaacgttc    2100
aatctgcgac gacgagatct cagctactgg gacgccggcc gaggccagtg ggtggtgccg    2160 gccgggagt ttaccgtcag cgtgggagcg agcagccggg atgtcaggct gacgggcagc    2220
ctgaccgcct ag                                                        2232
```

<210> SEQ ID NO 6
<211> LENGTH: 743
<212> TYPE: PRT
<213> ORGANISM: artificial
<220> FEATURE:
<223> OTHER INFORMATION: clone 59B8

<400> SEQUENCE: 6

```
Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
                20                  25                  30

Val Pro Pro Ala Gly Thr Pro Trp Gly Thr Ala Tyr Asp Lys Ala Lys
            35                  40                  45

Ala Ala Leu Ala Lys Leu Asn Leu Gln Asp Lys Val Gly Ile Val Ser
        50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Ile Arg Phe Gly Thr Gly Ser Thr Ala Phe Thr Pro Gly Val Gln Ala
            100                 105                 110

Ala Ser Thr Trp Asp Thr Glu Leu Met Arg Gln Arg Gly Glu Tyr Leu
        115                 120                 125

Gly Ala Glu Ala Lys Gly Cys Gly Ile His Val Leu Leu Gly Pro Val
130                 135                 140

Ala Gly Ala Leu Gly Lys Ile Pro His Gly Gly Arg Asn Trp Glu Gly
145                 150                 155                 160

Phe Gly Thr Asp Pro Tyr Leu Ala Gly Ile Ala Met Ala Glu Thr Ile
                165                 170                 175

Glu Gly Leu Gln Ser Ala Gly Val Gln Ala Cys Ala Lys His Tyr Ile
            180                 185                 190

Val Asn Glu Gln Glu Leu Asn Arg Glu Thr Ile Ser Ser Asp Val Asp
        195                 200                 205

Asp Arg Thr Met His Glu Leu Tyr Leu Trp Pro Phe Ala Asp Ala Val
    210                 215                 220

His Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
```

-continued

```
            275                 280                 285
Thr Asp Phe Asn Gly Asn Asn Arg Leu Trp Gly Pro Ala Leu Thr Asn
290                 295                 300
Ala Val Asn Ser Asn Gln Val Pro Thr Ser Arg Val Asp Asp Met Val
305                 310                 315                 320
Thr Arg Ile Leu Ala Ala Trp Tyr Leu Thr Gly Gln Asp Gln Ala Gly
            325                 330                 335
Tyr Pro Ser Phe Asn Ile Ser Arg Asn Val Gln Gly Asn His Lys Thr
            340                 345                 350
Asn Val Arg Ala Ile Ala Arg Asp Gly Ile Val Leu Leu Lys Asn Asp
            355                 360                 365
Ala Asn Ile Leu Pro Leu Lys Lys Pro Ala Ser Ile Ala Val Val Gly
370                 375                 380
Ser Ala Ala Ile Ile Gly Asn His Ala Arg Asn Ser Pro Ser Cys Asn
385                 390                 395                 400
Asp Lys Gly Cys Asp Asp Gly Ala Leu Gly Met Gly Trp Gly Ser Gly
            405                 410                 415
Ala Val Asn Tyr Pro Tyr Phe Val Ala Pro Tyr Asp Ala Leu Lys Thr
            420                 425                 430
Arg Ala Ser Ser Gln Gly Thr Gln Val Thr Leu Ser Asn Thr Asp Asn
            435                 440                 445
Thr Ser Ser Gly Ala Ser Ala Ala Arg Gly Lys Asp Val Ala Ile Val
450                 455                 460
Phe Ile Thr Ala Asp Ser Gly Glu Gly Tyr Ile Thr Val Glu Gly Asn
465                 470                 475                 480
Ala Gly Asp Arg Asn Asn Leu Asp Pro Trp His Asn Gly Asn Ala Leu
            485                 490                 495
Val Gln Ala Val Ala Gly Ala Asn Ser Asn Val Ile Val Val Val His
            500                 505                 510
Ser Val Gly Ala Ile Ile Leu Glu Gln Ile Leu Ala Leu Pro Gln Val
            515                 520                 525
Lys Ala Val Val Trp Ala Gly Leu Pro Ser Gln Glu Ser Gly Asn Ala
530                 535                 540
Leu Val Asp Val Leu Trp Gly Asp Val Ser Pro Ser Gly Lys Leu Val
545                 550                 555                 560
Tyr Thr Ile Ala Lys Ser Pro Asn Asp Tyr Asn Thr Arg Ile Val Ser
            565                 570                 575
Gly Gly Ser Asp Ser Phe Ser Glu Gly Leu Phe Ile Asp Tyr Lys His
            580                 585                 590
Phe Asp Asp Ala Lys Ile Glu Pro Arg Tyr Glu Phe Gly Phe Gly Leu
            595                 600                 605
Ser Tyr Thr Glu Phe Thr Tyr Ala Asp Leu Ser Val Thr Ser Thr Val
            610                 615                 620
Thr Ala Gly Pro Ala Ser Gly Glu Thr Ile Pro Gly Gly Ala Ala Asp
625                 630                 635                 640
Leu Trp Glu Thr Val Ala Thr Val Thr Ala Ser Ile Thr Asn Ser Gly
            645                 650                 655
Glu Val Glu Gly Ala Glu Val Ala Gln Leu Tyr Ile Thr Leu Pro Ser
            660                 665                 670
Ala Ala Pro Ser Thr Pro Pro Lys Gln Leu Arg Gly Phe Ala Lys Leu
            675                 680                 685
Lys Leu Glu Pro Gly Ala Ser Gly Val Ala Thr Phe Asn Leu Arg Arg
690                 695                 700
```

Arg Asp Leu Ser Tyr Trp Asp Ala Gly Arg Gly Gln Trp Val Val Pro
705                 710                 715                 720

Ala Gly Glu Phe Thr Val Ser Val Gly Ala Ser Ser Arg Asp Val Arg
            725                 730                 735

Leu Thr Gly Ser Leu Thr Ala
            740

<210> SEQ ID NO 7
<211> LENGTH: 2235
<212> TYPE: DNA
<213> ORGANISM: artificial
<220> FEATURE:
<223> OTHER INFORMATION: clone 164A2

<400> SEQUENCE: 7

```
atgcgttacc gaacagcagc tgcgctggca cttgccactg ggccctttgc tagggcagac      60
agtcactcaa catcgggggc ctcggctgag gcagttgtac ctcctgcagg gactccatgg     120
ggaaccgcgt acgacaaggc gaaggccgca ttggcaaagc tcaatctcca agataaggtc     180
ggcatcgtga gcggtgtcgg ctggaacggc ggtccttgcg ttggaaacac atctccggcc     240
tccaagatca gctatccatc gctatgcctt caagacggac ccctcggtgt tcgatactcg     300
acaggcagca cagcctttac gccgggcgtt caagcggcct cgacgtggga tgtcaatttg     360
atccgcgaac gtggacagtt catcggtgag gaggtgaagg cctcggggat tcatgtcata     420
cttggtcctg tggctgggcc gctgggaaag actccgcagg gcggtcgcaa ctgggagggc     480
ttcggtgtcg atccatatct cacgggcatt gccatgggtc aaaccatcaa cggcatccag     540
tcggtaggcg tgcaggcgac agcgaagcac tatatcctca cgagcagga gctcaatcga      600
gaaaccattt cgagcaaccc agatgaccga actctccatg agctgtatac ttggccattt     660
gccgacgcgg ttcacgccaa tgtcgcttct gtcatgtgct cgtacaacaa gatcaatggc     720
agctgggcct gcgaggatca gtacacgctg cagactgtgc tgaaagacca gctgggttc      780
ccaggctatg tcatgacgga ctggaacgca cagcacacga ctgtccaaag cgcgaattct     840
gggcttgaca tgtcaatgcc tggcacagac ttcaacggta caatcggct ctggggtcca      900
gctctcacca atgcggtaaa tagcaatcag gtccccacga gcagagtcga cgatatggtg     960
actcgtatcc tcgccgcatg gtacttgaca ggccaggacc aggcaggcta tccgtcgttc    1020
aacatcagca gaaatgttca aggaaaccac aagaccaatg tcagggcaat gccagggac     1080
ggcatcgttc tgctcaagaa tgacgccaac atcctgccgc tcaagaagcc cgctagcatt    1140
gccgtcgttg atctgccgc aatcattggt aaccacgcca gaaactcgcc ctcgtgcaac     1200
gacaaaggct cgacgacgg ggccttgggc atgggttggg gttccggcgc cgtcaactat     1260
ccgtacttcg tcgcgcccta cgatgccatc aataccgag cgtcttcgca gggcacccag     1320
gttaccttga gcaacaccga caacacgtcc tcaggcgcat ctgcagcaag aggaaaggac    1380
gtcgccatcg tcttcatcac cgccgactcg ggtgaaggct acatcaccgt ggagggcaac    1440
gcgggcgatc gcaacaacct ggatccgtgg cacaacggca atgccctggt ccaggcggtg    1500
gccggtgcca acagcaacgt cattgttgtt gtccactccg ttggcgccat cattctggag    1560
cagattcttg ctcttccgca ggtcaaggcc gttgtctggg cgggtcttcc ttctcaggag    1620
agcggcaatg cgctcgtcga cgtgctgtgg ggagatgtca gcccttctgg caagctggtg    1680
tacaccattg cgaagagccc caatgactat aacactcgca tcgtttccgg cggcagtgac    1740
agcttcagcg agggactgtt catcgactat aagcacttcg acgacgccaa tatcacgccg    1800
```

-continued

```
cggtacgagt tcggctatgg actgtcttac accaagttca actactcacg cctctccgtc    1860
ttgtcgaccg ccaagtctgg tcctgcgact ggggccgttg tgccgggagg cccgagtgat    1920
ctgttccaga atgtcgcgac agtcaccgtt gacatcgcaa actctggcca agtgactggt    1980
gccgaggtag cccagctgta catcacctac ccatcttcag cacccaggac ccctccgaag    2040
cagctgcgag gctttgccaa gctgaacctc acgcctggtc agagcggaac agcaacgttc    2100
aacatccgac gacgagatct cagctactgg gacacggctt cgcagaaatg ggtggtgccg    2160
tcggggtcgt ttggcatcag cgtgggagcg agcagccggg atatcaggct gacgagcact    2220
ctgtcggtag cgtag                                                     2235
```

<210> SEQ ID NO 8
<211> LENGTH: 744
<212> TYPE: PRT
<213> ORGANISM: artificial
<220> FEATURE:
<223> OTHER INFORMATION: clone 164A2

<400> SEQUENCE: 8

```
Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
                20                  25                  30

Val Pro Pro Ala Gly Thr Pro Trp Gly Thr Ala Tyr Asp Lys Ala Lys
            35                  40                  45

Ala Ala Leu Ala Lys Leu Asn Leu Gln Asp Lys Val Gly Ile Val Ser
        50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
    130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220

His Ala Asn Val Ala Ser Val Met Cys Ser Tyr Asn Lys Ile Asn Gly
225                 230                 235                 240

Ser Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
```

```
            275                 280                 285
Thr Asp Phe Asn Gly Asn Asn Arg Leu Trp Gly Pro Ala Leu Thr Asn
290                 295                 300
Ala Val Asn Ser Asn Gln Val Pro Thr Ser Arg Val Asp Asp Met Val
305                 310                 315                 320
Thr Arg Ile Leu Ala Ala Trp Tyr Leu Thr Gly Gln Asp Gln Ala Gly
            325                 330                 335
Tyr Pro Ser Phe Asn Ile Ser Arg Asn Val Gln Gly Asn His Lys Thr
            340                 345                 350
Asn Val Arg Ala Ile Ala Arg Asp Gly Ile Val Leu Leu Lys Asn Asp
        355                 360                 365
Ala Asn Ile Leu Pro Leu Lys Lys Pro Ala Ser Ile Ala Val Val Gly
        370                 375                 380
Ser Ala Ala Ile Ile Gly Asn His Ala Arg Asn Ser Pro Ser Cys Asn
385                 390                 395                 400
Asp Lys Gly Cys Asp Asp Gly Ala Leu Gly Met Gly Trp Gly Ser Gly
                405                 410                 415
Ala Val Asn Tyr Pro Tyr Phe Val Ala Pro Tyr Asp Ala Ile Asn Thr
            420                 425                 430
Arg Ala Ser Ser Gln Gly Thr Gln Val Thr Leu Ser Asn Thr Asp Asn
            435                 440                 445
Thr Ser Ser Gly Ala Ser Ala Ala Arg Gly Lys Asp Val Ala Ile Val
450                 455                 460
Phe Ile Thr Ala Asp Ser Gly Glu Gly Tyr Ile Thr Val Glu Gly Asn
465                 470                 475                 480
Ala Gly Asp Arg Asn Asn Leu Asp Pro Trp His Asn Gly Asn Ala Leu
                485                 490                 495
Val Gln Ala Val Ala Gly Ala Asn Ser Asn Val Ile Val Val Val His
            500                 505                 510
Ser Val Gly Ala Ile Ile Leu Glu Gln Ile Leu Ala Leu Pro Gln Val
            515                 520                 525
Lys Ala Val Val Trp Ala Gly Leu Pro Ser Gln Glu Ser Gly Asn Ala
        530                 535                 540
Leu Val Asp Val Leu Trp Gly Asp Val Ser Pro Ser Gly Lys Leu Val
545                 550                 555                 560
Tyr Thr Ile Ala Lys Ser Pro Asn Asp Tyr Asn Thr Arg Ile Val Ser
                565                 570                 575
Gly Gly Ser Asp Ser Phe Ser Glu Gly Leu Phe Ile Asp Tyr Lys His
            580                 585                 590
Phe Asp Asp Ala Asn Ile Thr Pro Arg Tyr Glu Phe Gly Tyr Gly Leu
            595                 600                 605
Ser Tyr Thr Lys Phe Asn Tyr Ser Arg Leu Ser Val Leu Ser Thr Ala
            610                 615                 620
Lys Ser Gly Pro Ala Thr Gly Ala Val Val Pro Gly Gly Pro Ser Asp
625                 630                 635                 640
Leu Phe Gln Asn Val Ala Thr Val Thr Val Asp Ile Ala Asn Ser Gly
            645                 650                 655
Gln Val Thr Gly Ala Glu Val Ala Gln Leu Tyr Ile Thr Tyr Pro Ser
            660                 665                 670
Ser Ala Pro Arg Thr Pro Pro Lys Gln Leu Arg Gly Phe Ala Lys Leu
        675                 680                 685
Asn Leu Thr Pro Gly Gln Ser Gly Thr Ala Thr Phe Asn Ile Arg Arg
        690                 695                 700
```

```
Arg Asp Leu Ser Tyr Trp Asp Thr Ala Ser Gln Lys Trp Val Pro
705                 710                 715                 720

Ser Gly Ser Phe Gly Ile Ser Val Gly Ala Ser Ser Arg Asp Ile Arg
            725                 730                 735

Leu Thr Ser Thr Leu Ser Val Ala
            740

<210> SEQ ID NO 9
<211> LENGTH: 2235
<212> TYPE: DNA
<213> ORGANISM: artificial
<220> FEATURE:
<223> OTHER INFORMATION: clone 100B11

<400> SEQUENCE: 9
```

| | | | | | |
|---|---|---|---|---|---|
| atgcgttacc | gaacagcagc | tgcgctggca | cttgccactg | ggccctttgc | tagggcagac |   60 |
| agtcactcaa | catcggggc | ctcggctgag | gcagttgtac | ctcctgcagg | gactccatgg |  120 |
| ggaaccgcgt | acgacaaggc | gaaggccgca | ttggcaaagc | tcaatctcca | agataaggtc |  180 |
| ggcatcgtga | gcggtgtcgg | ctggaacggc | ggtccttgcg | ttggaaacac | atctccggcc |  240 |
| tccaagatca | gctatccatc | gctatgcctt | caagacggac | ccctcggtat | ccgattcggc |  300 |
| acaggcagca | cagcctttac | gccgggcgtt | caagcggcct | cgacgtggga | taccgagttg |  360 |
| atgcgccagc | gtggagagta | cctgggtgcc | gaggccaagg | gctgcgggat | tcatgtcctg |  420 |
| cttggtcctg | tggctgggcc | gctgggaaag | actccgcagg | gcggtcgcaa | ctgggagggc |  480 |
| ttcggtgtcg | atccatatct | cacgggcatt | gccatggccg | agacaatcga | gggcctgcag |  540 |
| tcggccggcg | tgcaggcgtg | cgcgaagcac | tatatcgtca | cgagcagga | gctcaatcga |  600 |
| gaaaccattt | cgagcgacgt | cgatgaccga | actatgcatg | agctgtatct | gtggccattt |  660 |
| gccgacgcgg | ttcaggccaa | tgtcgcttct | gtcatgtgct | cgtacaacaa | gatcaatggc |  720 |
| agctgggcct | gcgaggatca | gtacacgctg | cagactgtgc | tgaaagacca | gctgggggttc |  780 |
| ccaggctatg | tcatgacgga | ctggaacgca | cagcacacga | ctgtccaaag | cgcgaattct |  840 |
| gggcttgaca | tgtcaatgcc | tggcacagac | ttcaacggta | caatcggct | ctggggtcca |  900 |
| gctctcacca | atgcggtaaa | tagcaatcag | gtccccacga | gcagagtcga | cgatatggtg |  960 |
| actcgtatcc | tcgccgcatg | gtacttgaca | ggccaggacc | aggcaggcta | tccgtcgttc | 1020 |
| aacatcagca | gaaatgttca | aggaaaccac | aagaccaatg | tcagggcaat | tgccagggac | 1080 |
| ggcatcgttc | tgctcaagaa | tgacgccaac | atcctgccgc | tcaagaagcc | cgctagcatt | 1140 |
| gccgtcgttg | gatctgccgc | aatcattggt | aaccacgcca | gaaactcgcc | ctcgtgcaac | 1200 |
| gacaaaggct | gcgacgacgg | ggccttgggc | atgggttggg | gttccggcgc | cgtcaactat | 1260 |
| ccgtacttcg | tcgcgcccta | cgatgccatc | aataccgag | cgtcttcgca | gggcacccag | 1320 |
| gttaccttga | gcaacaccga | caacacgtcc | tcaggcgcat | ctgcagcaag | aggaaaggac | 1380 |
| gtcgccatcg | tcttcatcac | cgccgactcg | ggtgaaggct | acatcaccgt | ggagggcaac | 1440 |
| gcgggcgatc | gcaacaacct | ggatccgtgg | cacaacggca | atgccctggt | ccaggcggtg | 1500 |
| gccggtgcca | acagcaacgt | cattgttgtt | gtccactccg | ttggcgccat | cattctggag | 1560 |
| cagattcttg | ctcttccgca | ggtcaaggcc | gttgtctggg | cgggtcttcc | ttctcaggag | 1620 |
| agcggcaatg | cgctcgtcga | cgtgctgtgg | ggagatgtca | gcccttctgg | caagctggtg | 1680 |
| tacaccattg | cgaagagccc | caatgactat | aacactcgca | tcgtttccgg | cggcagtgac | 1740 |
| agcttcagcg | agggactgtt | catcgactat | aagcacttcg | acgacgccaa | tatcacgccg | 1800 |

```
cggtacgagt tcggctatgg actgtcttac accaagttca actactcacg cctctccgtc    1860
ttttcgaccg ccaagtctgg tcctgcgact ggggccgttg tgccgggagg cccgagtgat    1920
ctgttccaga atgtcgcgac agtcaccgtt gacatcgcaa actctggcca agtgactggt    1980
gccgaggtag cccagctgta catcacctac ccatcttcag cacccaggac ccctccgaag    2040
cagctgcgag gctttgccaa gctgaacctc acgcctggtc agagcggaac agcaacgttc    2100
aacatccgac gacgagatct cagctactgg gacacggctt cgcagaaatg ggtggtgccg    2160
tcggggtcgt ttggcatcag cgtgggagcg agcagccggg atatcaggct gacgagcact    2220
ctgtcggtag cgtag                                                     2235
```

<210> SEQ ID NO 10
<211> LENGTH: 744
<212> TYPE: PRT
<213> ORGANISM: artificial
<220> FEATURE:
<223> OTHER INFORMATION: clone 100B11

<400> SEQUENCE: 10

```
Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
            20                  25                  30

Val Pro Pro Ala Gly Thr Pro Trp Gly Thr Ala Tyr Asp Lys Ala Lys
        35                  40                  45

Ala Ala Leu Ala Lys Leu Asn Leu Gln Asp Lys Val Gly Ile Val Ser
    50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Ile Arg Phe Gly Thr Gly Ser Thr Ala Phe Thr Pro Gly Val Gln Ala
            100                 105                 110

Ala Ser Thr Trp Asp Thr Glu Leu Met Arg Gln Arg Gly Glu Tyr Leu
        115                 120                 125

Gly Ala Glu Ala Lys Gly Cys Gly Ile His Val Leu Leu Gly Pro Val
    130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Ala Glu Thr Ile
                165                 170                 175

Glu Gly Leu Gln Ser Ala Gly Val Gln Ala Cys Ala Lys His Tyr Ile
            180                 185                 190

Val Asn Glu Gln Glu Leu Asn Arg Glu Thr Ile Ser Ser Asp Val Asp
        195                 200                 205

Asp Arg Thr Met His Glu Leu Tyr Leu Trp Pro Phe Ala Asp Ala Val
    210                 215                 220

Gln Ala Asn Val Ala Ser Val Met Cys Ser Tyr Asn Lys Ile Asn Gly
225                 230                 235                 240

Ser Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
```

-continued

```
                275                 280                 285
Thr Asp Phe Asn Gly Asn Asn Arg Leu Trp Gly Pro Ala Leu Thr Asn
290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
                340                 345                 350

Asn Val Arg Ala Ile Ala Arg Asp Gly Ile Val Leu Leu Lys Asn Asp
                355                 360                 365

Ala Asn Ile Leu Pro Leu Lys Lys Pro Ala Ser Ile Ala Val Val Gly
370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
                420                 425                 430

Arg Ala Ser Ser Gln Gly Thr Gln Val Thr Leu Ser Asn Thr Asp Asn
                435                 440                 445

Thr Ser Ser Gly Ala Ser Ala Ala Arg Gly Lys Asp Val Ala Ile Val
450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val Val His
                500                 505                 510

Ser Val Gly Ala Ile Ile Leu Glu Gln Ile Leu Ala Leu Pro Gln Val
                515                 520                 525

Lys Ala Val Val Trp Ala Gly Leu Pro Ser Gln Glu Ser Gly Asn Ala
530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
                580                 585                 590

Phe Asp Asp Ala Asn Ile Thr Pro Arg Tyr Glu Phe Gly Tyr Gly Leu
                595                 600                 605

Ser Tyr Thr Lys Phe Asn Tyr Ser Arg Leu Ser Val Phe Ser Thr Ala
                610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
                660                 665                 670

Ser Ala Pro Arg Thr Pro Pro Lys Gln Leu Arg Gly Phe Ala Lys Leu
                675                 680                 685

Asn Leu Thr Pro Gly Gln Ser Gly Thr Ala Thr Phe Asn Ile Arg Arg
690                 695                 700
```

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
            725                 730                 735

Leu Thr Ser Thr Leu Ser Val Ala
            740

<210> SEQ ID NO 11
<211> LENGTH: 2235
<212> TYPE: DNA
<213> ORGANISM: artificial
<220> FEATURE:
<223> OTHER INFORMATION: clone 115E1

<400> SEQUENCE: 11

| | | | | | |
|---|---|---|---|---|---|
| atgcgttacc | gaacagcagc | tgcgctggca | cttgccactg | ggcccttttgc | tagggcagac | 60 |
| agtcactcaa | catcggggc | ctcggctgag | gcagttgtac | ctcctgcagg | gactccatgg | 120 |
| ggaaccgcgt | acgacaaggc | gaaggccgca | ttggcaaagc | tcaatctcca | agataaggtc | 180 |
| ggcatcgtga | gcggtgtcgg | ctggaacggc | ggtccttgcg | ttggaaacac | atctccggcc | 240 |
| tccaagatca | gctatccatc | gctatgcctt | caagacggac | ccctcggtat | ccgattcggc | 300 |
| acaggcagca | cagcctttac | gccgggcgtt | caagcggcct | cgacgtggga | tgtcaatttg | 360 |
| atccgcgaac | gtggacagtt | catcggtgag | gaggtgaagg | cctcggggat | tcatgtcata | 420 |
| cttggtcctg | tggctgggcc | gctgggaaag | atcccgcacg | gcggtcgcaa | ctgggagggc | 480 |
| ttcggtgtcg | atccatatct | cacgggcatt | gccatggccg | agacaatcga | gggcctgcag | 540 |
| tcggccggcg | tgcaggcgtg | cgcgaagcac | tatatcctca | acgagcagga | gctcaatcga | 600 |
| gaaaccattt | cgagcaaccc | agatgaccga | actctccatg | agctgtatac | ttggccattt | 660 |
| gccgacgcgg | ttcacgccaa | tgtcgcttct | gtcatgtgct | cgtacaacaa | gatcaatggc | 720 |
| agctgggcct | gcgaggatca | gtacacgctg | cagactgtgc | tgaaagacca | gctggggttc | 780 |
| ccaggctatg | tcatgacgga | ctggaacgca | cagcacacga | ctgtccaaag | cgcgaattct | 840 |
| gggcttgaca | tgtcaatgcc | tggcacagac | ttcaacggta | caatcggct | ctggggtcca | 900 |
| gctctcacca | atgcggtaaa | tagcaatcag | gtccccacga | gcagagtcga | cgatatggtg | 960 |
| actcgtatcc | tcgccgcatg | gtacttgaca | ggccaggacc | aggcaggcta | tccgtcgttc | 1020 |
| aacatcagca | gaaatgttca | aggaaaccac | aagaccaatg | tcagggcaat | tgccagggac | 1080 |
| ggcatcgttc | tgctcaagaa | tgacgccaac | atcctgccgc | tcaagaagcc | cgctagcatt | 1140 |
| gccgtcgttg | gatctgccgc | aatcattggt | aaccacgcca | gaaactcgcc | ctcgtgcaac | 1200 |
| gacaaaggct | gcgacgacgg | ggccttgggc | atgggttggg | gttccggcgc | cgtcaactat | 1260 |
| ccgtacttcg | tcgcgcccta | cgatgccatc | aataccgag | cgtcttcgca | gggcacccag | 1320 |
| gttaccttga | gcaacaccga | caacacgtcc | tcaggcgcat | ctgcagcaag | aggaaaggac | 1380 |
| gtcgccatcg | tcttcatcac | cgccgactcg | ggtgaaggct | acatcaccgt | ggagggcaac | 1440 |
| gcgggcgatc | gcaacaacct | ggatccgtgg | cacaacggca | atgccctggt | ccaggcggtg | 1500 |
| gccggtgcca | acagcaacgt | cattgttgtt | gtccactccg | ttggcgccat | cattctggag | 1560 |
| cagattcttg | ctcttccgca | ggtcaaggcc | gttgtctggg | cgggtcttcc | ttctcaggag | 1620 |
| agcggcaatg | cgctcgtcga | cgtgctgtgg | ggagatgtca | gcccttctgg | caagctggtg | 1680 |
| tacaccattg | cgaagagccc | caatgactat | aacactcgca | tcgtttccgg | cggcagtgac | 1740 |
| agcttcagcg | agggactgtt | catcgactat | aagcacttcg | acgacgccaa | tatcacgccg | 1800 |

-continued

```
cggtacgagt tcggctatgg actgtcttac accaagttca actactcacg cctctccgtc    1860
ttgtcgaccg ccaagtctgg tcctgcgact ggggccgttg tgccgggagg cccgagtgat    1920
ctgttccaga atgtcgcgac agtcaccgtt gacatcgcaa actctggcca agtgactggt    1980
gccgaggtag cccagctgta catcacctac ccatcttcag cacccaggac ccctccgaag    2040
cagctgcgag gctttgccaa gctgaacctc acgcctggtc agagcggaac agcaacgttc    2100
aacatccgac gacgagatct cagctactgg gacacggctt cgcagaaatg ggtggtgccg    2160
tcggggtcgt ttggcatcag cgtgggagcg agcagccggg atatcaggct gacgagcact    2220
ctgtcggtag cgtag                                                    2235
```

<210> SEQ ID NO 12
<211> LENGTH: 744
<212> TYPE: PRT
<213> ORGANISM: artificial
<220> FEATURE:
<223> OTHER INFORMATION: clone 115E1

<400> SEQUENCE: 12

```
Met Arg Tyr Arg Thr Ala Ala Leu Ala Leu Ala Thr Gly Pro Phe
 1               5                  10                  15

Ala Arg Ala Asp Ser His Ser Thr Ser Gly Ala Ser Ala Glu Ala Val
                20                  25                  30

Val Pro Pro Ala Gly Thr Pro Trp Gly Thr Ala Tyr Asp Lys Ala Lys
            35                  40                  45

Ala Ala Leu Ala Lys Leu Asn Leu Gln Asp Lys Val Gly Ile Val Ser
        50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Ile Arg Phe Gly Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
    130                 135                 140

Ala Gly Pro Leu Gly Lys Ile Pro His Gly Gly Arg Asn Trp Glu Gly
145                 150                 155                 160

Phe Gly Val Asp Pro Tyr Leu Thr Gly Ile Ala Met Ala Glu Thr Ile
                165                 170                 175

Glu Gly Leu Gln Ser Ala Gly Val Gln Ala Cys Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220

His Ala Asn Val Ala Ser Val Met Cys Ser Tyr Asn Lys Ile Asn Gly
225                 230                 235                 240

Ser Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
```

-continued

```
                    275                 280                 285
Thr Asp Phe Asn Gly Asn Asn Arg Leu Trp Gly Pro Ala Leu Thr Asn
290                 295                 300
Ala Val Asn Ser Asn Gln Val Pro Thr Ser Arg Val Asp Asp Met Val
305                 310                 315                 320
Thr Arg Ile Leu Ala Ala Trp Tyr Leu Thr Gly Gln Asp Gln Ala Gly
                325                 330                 335
Tyr Pro Ser Phe Asn Ile Ser Arg Asn Val Gln Gly Asn His Lys Thr
                340                 345                 350
Asn Val Arg Ala Ile Ala Arg Asp Gly Ile Val Leu Leu Lys Asn Asp
                355                 360                 365
Ala Asn Ile Leu Pro Leu Lys Lys Pro Ala Ser Ile Ala Val Val Gly
370                 375                 380
Ser Ala Ala Ile Ile Gly Asn His Ala Arg Asn Ser Pro Ser Cys Asn
385                 390                 395                 400
Asp Lys Gly Cys Asp Asp Gly Ala Leu Gly Met Gly Trp Gly Ser Gly
                405                 410                 415
Ala Val Asn Tyr Pro Tyr Phe Val Ala Pro Tyr Asp Ala Ile Asn Thr
                420                 425                 430
Arg Ala Ser Ser Gln Gly Thr Gln Val Thr Leu Ser Asn Thr Asp Asn
                435                 440                 445
Thr Ser Ser Gly Ala Ser Ala Ala Arg Gly Lys Asp Val Ala Ile Val
450                 455                 460
Phe Ile Thr Ala Asp Ser Gly Glu Gly Tyr Ile Thr Val Glu Gly Asn
465                 470                 475                 480
Ala Gly Asp Arg Asn Asn Leu Asp Pro Trp His Asn Gly Asn Ala Leu
                485                 490                 495
Val Gln Ala Val Ala Gly Ala Asn Ser Asn Val Ile Val Val Val His
                500                 505                 510
Ser Val Gly Ala Ile Ile Leu Glu Gln Ile Leu Ala Leu Pro Gln Val
                515                 520                 525
Lys Ala Val Val Trp Ala Gly Leu Pro Ser Gln Glu Ser Gly Asn Ala
530                 535                 540
Leu Val Asp Val Leu Trp Gly Asp Val Ser Pro Ser Gly Lys Leu Val
545                 550                 555                 560
Tyr Thr Ile Ala Lys Ser Pro Asn Asp Tyr Asn Thr Arg Ile Val Ser
                565                 570                 575
Gly Gly Ser Asp Ser Phe Ser Glu Gly Leu Phe Ile Asp Tyr Lys His
                580                 585                 590
Phe Asp Asp Ala Asn Ile Thr Pro Arg Tyr Glu Phe Gly Tyr Gly Leu
                595                 600                 605
Ser Tyr Thr Lys Phe Asn Tyr Ser Arg Leu Ser Val Leu Ser Thr Ala
                610                 615                 620
Lys Ser Gly Pro Ala Thr Gly Ala Val Val Pro Gly Gly Pro Ser Asp
625                 630                 635                 640
Leu Phe Gln Asn Val Ala Thr Val Thr Val Asp Ile Ala Asn Ser Gly
                645                 650                 655
Gln Val Thr Gly Ala Glu Val Ala Gln Leu Tyr Ile Thr Tyr Pro Ser
                660                 665                 670
Ser Ala Pro Arg Thr Pro Lys Gln Leu Arg Gly Phe Ala Lys Leu
                675                 680                 685
Asn Leu Thr Pro Gly Gln Ser Gly Thr Ala Thr Phe Asn Ile Arg Arg
690                 695                 700
```

-continued

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
            725                 730                 735

Leu Thr Ser Thr Leu Ser Val Ala
        740

<210> SEQ ID NO 13
<211> LENGTH: 2259
<212> TYPE: DNA
<213> ORGANISM: artificial
<220> FEATURE:
<223> OTHER INFORMATION: clone 149G7

<400> SEQUENCE: 13

| | | | | | |
|---|---|---|---|---|---|
| atgcgttacc | gaacagcagc | tgcgctggca | cttgccactg | ggcccttttgc | tagggcagac | 60 |
| agtcactcaa | catcgggggc | ctcggctgag | gcagagacaa | gcgagaagca | ggcccgacag | 120 |
| gccggcagcg | gcttcgccgc | ctgggacgcc | gcgtacagcc | aggcgagcac | cgcattgagc | 180 |
| aagctcagcc | agcaagataa | ggtcaacatc | gtgaccggtg | tcggctggaa | caagggtcct | 240 |
| tgcgttggaa | acacaccggc | catcgccagc | atcggctatc | cacagctatg | ccttcaagac | 300 |
| ggaccctcg | gtatccgatt | cggcacaggc | agcacagcct | ttacgccggg | cgttcaagcg | 360 |
| gcctcgacgt | gggatgtcga | gttgatccgc | cagcgtgggg | tctacctggg | tgccgaggcc | 420 |
| cgaggcgtcg | gggtccatgt | cctgcttggt | cctgtggctg | gccgctgggg | aaagactccg | 480 |
| cagggcggtc | gcaactggga | gggcttcggt | gtcgatccat | atctcacggg | cattgccatg | 540 |
| agcgagacaa | tcgagggcat | ccagtcgaac | ggcgtgcagg | cgtgcgcgaa | gcactatatc | 600 |
| ctcaacgagc | aggagctcaa | tcgagaaacc | atttcgagca | acccagatga | ccgaactctc | 660 |
| catgagctgt | atacttggcc | atttgccgac | gcggttcacg | ccaatgtcgc | ttctgtcatg | 720 |
| tgctcgtaca | acaagatcaa | tggcagctgg | gcctgcgagg | atcagtacac | gctgcagact | 780 |
| gtgctgaaag | accagctggg | gttcccaggc | tatgtcatga | cggactggaa | cgcacagcac | 840 |
| acgactgtcc | aaagcgcgaa | ttctgggctt | gacatgtcaa | tgcctggcac | agacttcaac | 900 |
| ggtaacaatc | ggctctgggg | tccagctctc | accaatgcgg | taaatagcaa | tcaggtcccc | 960 |
| acgagcagag | tcgacgatat | ggtgactcgt | atcctcgccg | catggtactt | gacaggccag | 1020 |
| gaccaggcag | gctatccgtc | gttcaacatc | agcagaaatg | ttcaaggaaa | ccacaagacc | 1080 |
| aatgtcaggg | caattgccag | ggacggcatc | gttctgctca | gaatgacgc | caacatcctg | 1140 |
| ccgctcaaga | agcccgctag | cattgccgtc | gttggatctg | ccgcaatcat | tggtaaccac | 1200 |
| gccagaaact | cgccctcgtg | caacgacaaa | ggctgcgacg | acgggggcctt | gggcatgggt | 1260 |
| tggggttccg | gcgccgtcaa | ctatccgtac | ttcgtcgcgc | cctacgatgc | catcaatacc | 1320 |
| agagcgtctt | cgcagggcac | ccaggttacc | ttgagcaaca | ccgacaacac | gtcctcaggc | 1380 |
| gcatctgcag | caagaggaaa | ggacgtcgcc | atcgtcttca | tcaccgccga | ctcgggtgaa | 1440 |
| ggctacatca | ccgtggaggg | caacgcgggc | gatcgcaaca | acctggatcc | gtggcacaac | 1500 |
| ggcaatgccc | tggtccaggc | ggtggccggt | gccaacagca | acgtcattgt | tgttgtccac | 1560 |
| tccgttggcg | ccatcattct | ggagcagatt | cttgctcttc | gcaggtcaa | ggccgttgtc | 1620 |
| tgggcgggtc | ttccttctca | ggagagcggc | aatgcgctcg | tcgacgtgct | gtggggagat | 1680 |
| gtcagccctt | ctggcaagct | ggtgtacacc | attgcgaaga | gccccaatga | ctataacact | 1740 |
| cgcatcgttt | ccggcggcag | tgacagcttc | agcgagggac | tgttcatcga | ctataagcac | 1800 |

```
ttcgacgacg ccaatatcac gccgcggtac gagttcggct atggactgtc ttacaccaag    1860
ttcaactact cacgcctctc cgtcttgtcg accgccaagt ctggtcctgc gactggggcc    1920
gttgtgccgg gaggcccgag tgatctgttc cagaatgtcg cgacagtcac cgttgacatc    1980
gcaaactctg gccaagtgac tggtgccgag gtagcccagc tgtacatcac ctacccatct    2040
tcagcaccca ggacccctcc gaagcagctg cgaggctttg ccaagctgaa cctcacgcct    2100
ggtcagagcg aacagcaac gttcaacatc cgacgacgag atctcagcta ctgggacacg     2160
gcttcgcaga aatgggtggt gccgtcgggg tcgtttggca tcagcgtggg agcgagcagc    2220
cgggatatca ggctgacgag cactctgtcg gtagcgtag                            2259
```

<210> SEQ ID NO 14
<211> LENGTH: 752
<212> TYPE: PRT
<213> ORGANISM: artificial
<220> FEATURE:
<223> OTHER INFORMATION: clone 149G7

<400> SEQUENCE: 14

```
Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Glu
            20                  25                  30

Thr Ser Glu Lys Gln Ala Arg Gln Ala Gly Ser Gly Phe Ala Ala Trp
        35                  40                  45

Asp Ala Ala Tyr Ser Gln Ala Ser Thr Ala Leu Ser Lys Leu Ser Gln
    50                  55                  60

Gln Asp Lys Val Asn Ile Val Thr Gly Val Gly Trp Asn Lys Gly Pro
65                  70                  75                  80

Cys Val Gly Asn Thr Pro Ala Ile Ala Ser Ile Gly Tyr Pro Gln Leu
                85                  90                  95

Cys Leu Gln Asp Gly Pro Leu Gly Ile Arg Phe Gly Thr Gly Ser Thr
            100                 105                 110

Ala Phe Thr Pro Gly Val Gln Ala Ala Ser Thr Trp Asp Val Glu Leu
        115                 120                 125

Ile Arg Gln Arg Gly Val Tyr Leu Gly Ala Glu Ala Arg Gly Val Gly
    130                 135                 140

Val His Val Leu Leu Gly Pro Val Ala Gly Pro Leu Gly Lys Thr Pro
145                 150                 155                 160

Gln Gly Gly Arg Asn Trp Glu Gly Phe Gly Val Asp Pro Tyr Leu Thr
                165                 170                 175

Gly Ile Ala Met Ser Glu Thr Ile Glu Gly Ile Gln Ser Asn Gly Val
            180                 185                 190

Gln Ala Cys Ala Lys His Tyr Ile Leu Asn Glu Gln Glu Leu Asn Arg
        195                 200                 205

Glu Thr Ile Ser Ser Asn Pro Asp Asp Arg Thr Leu His Glu Leu Tyr
    210                 215                 220

Thr Trp Pro Phe Ala Asp Ala Val His Ala Asn Val Ala Ser Val Met
225                 230                 235                 240

Cys Ser Tyr Asn Lys Ile Asn Gly Ser Trp Ala Cys Glu Asp Gln Tyr
                245                 250                 255

Thr Leu Gln Thr Val Leu Lys Asp Gln Leu Gly Phe Pro Gly Tyr Val
            260                 265                 270

Met Thr Asp Trp Asn Ala Gln His Thr Thr Val Gln Ser Ala Asn Ser
```

```
              275                 280                 285
Gly Leu Asp Met Ser Met Pro Gly Thr Asp Phe Asn Gly Asn Asn Arg
290                 295                 300

Leu Trp Gly Pro Ala Leu Thr Asn Ala Val Asn Ser Asn Gln Val Pro
305                 310                 315                 320

Thr Ser Arg Val Asp Asp Met Val Thr Arg Ile Leu Ala Ala Trp Tyr
                325                 330                 335

Leu Thr Gly Gln Asp Gln Ala Gly Tyr Pro Ser Phe Asn Ile Ser Arg
                340                 345                 350

Asn Val Gln Gly Asn His Lys Thr Asn Val Arg Ala Ile Ala Arg Asp
                355                 360                 365

Gly Ile Val Leu Leu Lys Asn Asp Ala Asn Ile Leu Pro Leu Lys Lys
                370                 375                 380

Pro Ala Ser Ile Ala Val Val Gly Ser Ala Ala Ile Ile Gly Asn His
385                 390                 395                 400

Ala Arg Asn Ser Pro Ser Cys Asn Asp Lys Gly Cys Asp Asp Gly Ala
                405                 410                 415

Leu Gly Met Gly Trp Gly Ser Gly Ala Val Asn Tyr Pro Tyr Phe Val
                420                 425                 430

Ala Pro Tyr Asp Ala Ile Asn Thr Arg Ala Ser Ser Gln Gly Thr Gln
                435                 440                 445

Val Thr Leu Ser Asn Thr Asp Asn Thr Ser Ser Gly Ala Ser Ala Ala
                450                 455                 460

Arg Gly Lys Asp Val Ala Ile Val Phe Ile Thr Ala Asp Ser Gly Glu
465                 470                 475                 480

Gly Tyr Ile Thr Val Glu Gly Asn Ala Gly Asp Arg Asn Asn Leu Asp
                485                 490                 495

Pro Trp His Asn Gly Asn Ala Leu Val Gln Ala Val Ala Gly Ala Asn
                500                 505                 510

Ser Asn Val Ile Val Val His Ser Val Gly Ala Ile Ile Leu Glu
                515                 520                 525

Gln Ile Leu Ala Leu Pro Gln Val Lys Ala Val Val Trp Ala Gly Leu
530                 535                 540

Pro Ser Gln Glu Ser Gly Asn Ala Leu Val Asp Val Leu Trp Gly Asp
545                 550                 555                 560

Val Ser Pro Ser Gly Lys Leu Val Tyr Thr Ile Ala Lys Ser Pro Asn
                565                 570                 575

Asp Tyr Asn Thr Arg Ile Val Ser Gly Gly Ser Asp Ser Phe Ser Glu
                580                 585                 590

Gly Leu Phe Ile Asp Tyr Lys His Phe Asp Asp Ala Asn Ile Thr Pro
                595                 600                 605

Arg Tyr Glu Phe Gly Tyr Gly Leu Ser Tyr Thr Lys Phe Asn Tyr Ser
                610                 615                 620

Arg Leu Ser Val Leu Ser Thr Ala Lys Ser Gly Pro Ala Thr Gly Ala
625                 630                 635                 640

Val Val Pro Gly Gly Pro Ser Asp Leu Phe Gln Asn Val Ala Thr Val
                645                 650                 655

Thr Val Asp Ile Ala Asn Ser Gly Gln Val Thr Gly Ala Glu Val Ala
                660                 665                 670

Gln Leu Tyr Ile Thr Tyr Pro Ser Ser Ala Pro Arg Thr Pro Pro Lys
                675                 680                 685

Gln Leu Arg Gly Phe Ala Lys Leu Asn Leu Thr Pro Gly Gln Ser Gly
                690                 695                 700
```

```
Thr Ala Thr Phe Asn Ile Arg Arg Arg Asp Leu Ser Tyr Trp Asp Thr
705                 710                 715                 720

Ala Ser Gln Lys Trp Val Val Pro Ser Gly Ser Phe Gly Ile Ser Val
            725                 730                 735

Gly Ala Ser Ser Arg Asp Ile Arg Leu Thr Ser Thr Leu Ser Val Ala
        740                 745                 750

<210> SEQ ID NO 15
<211> LENGTH: 2181
<212> TYPE: DNA
<213> ORGANISM: Chaetomium globosum

<400> SEQUENCE: 15
atgacgacgc tccgcaactt tgcgctgctc gcagcggcgg tgcttgcgcg ggtcgaggcc      60
ctcgaggccg ccgactgggc tgcggctgag gcctcagcca aaaccgcact ggcaaagatg     120
tcacaacaag acaaaatcag cattgtgacg ggcatcggct gggacaaggg tccctgtgtc     180
ggcaacacgg ccgccatcaa ctcgatcaac tacccgcagc tctgcctaca ggacggcccg     240
ctcgggatcc gcttcggcac cggctcgacg gccttcaccc cgggcgtcca agccgcctcg     300
acatgggata ccgagctgat gcgccagcgc ggcgagtacc tcggggccga ggccaagggg     360
tgcggcatcc acgtgttgct ggggcccgtg gccggggcac tgggcaagat cccgcacggc     420
gggcgcaact gggaaggatt cggacggac ccgtacctgg cgggcatcgc catggccgag     480
acgatcgagg ggctgcagtc ggcgggggtg caggcgtgcg ccaagcacta catcgtcaac     540
gagcaggagc tcaaccgcga gaccatcagc agcgacgtcg acgaccgcac catgcacgag     600
ctgtacctgt ggcccttcgc cgacgccgtg cacgccaacg tggccagcgt catgtgcagc     660
tacaacaaga tcaacggctc gtggggctgc gagaacgacc acgcccaaaa cggcctgctc     720
aagaaggagc tcggcttcaa gggttacgtc gtcagcgact ggaacgcgca gcacacgacc     780 gacgcgccg ccaacaacgg catggacatg accatgccgg cagcgactac aacggcaac      840 aacgtgctct ggggcccgca gctcagcaac gccgtcaaca gcaacgggt ctcgcgcgac     900 cggctcgacg acatggccaa acgcatcctc acctcatggt acctcctggg ccagaactcg     960
ggctacccca acatcaacat caacgccaac gtgcagggca accacaagga gaacgtgcgg    1020
gcggtggcgc gcgacggcat cgtgctgctc aagaacgacg agggcgtgct cccgctgaag    1080
aagccaggca aggtggctct cgtcggatcg gcggcctcgg tcaacagcgc gggccccaac    1140
gcgtgcgtcg acaagggctg caacacgggc gcgctcggca tgggctgggg gtccgggtcc    1200
gtcaactacc cctactttgt ggcgccctac gacgcgctca gacgcgcgc ccaggccgac     1260 ggcaccacgc tcagcctgca caactcggac tcgaccaacg cgtatcgggg cgtggtgtcg    1320
ggcgccgacg tggccatcgt ggtgatcacg gcggactcgg gcgagggcta catcacggtc    1380
gagggccacg ccggcgaccg caaccacctg gaccgtggc acgacggcaa cgcgctggtt     1440
aaggcggtgg ccgcggccaa caagaacacc atcgtggtag tgcacagcac agggcccatc    1500
atcctcgaga ccatcctggc gacggagggt gtcaaggcgg ttgtgtgggc cggcctgccg    1560
agtcaggaga cggcaacgc gctagttgac gttttgtacg gcctgacttc gccctcaggc     1620
aaactggtct actccatcgc caagcgcccc gaggactatg gcacggcccc ctccaagggc    1680
agtaacgaca agttcaccga aggcctgttt gtcgactacc ggcactttga caacgccaag    1740
attgagccgc ggtacgagtt tggctttggt ttgtcctaca ccgaattcac ctacgccgac    1800
ctctccgtca cttccaccgt aacggccggc cccgcctcag gcgagaccat acccggcggc    1860
```

```
gcggccgacc tctgggagac tgtcgcaacg gtcacggcgt ccatcacgaa cagcggcgag    1920
gtggagggcg ccgaggtggc gcagctgtac atcacgctgc cgtcggcggc ccctcgacg     1980 ccgcccaagc agctgcgcgg gttcgccaag ctcaagctcg agccggggc gtcgggcgtc     2040 gcgaccttca acctgcgccg tcgcgatctg agttattggg atgccggcg cggccagtgg     2100 gtggtgccgg cgggcgagtt tacggtttcg gttggtgcga gttcgaggga tgtgcgcttg    2160
acggggagct tgactgctta g                                              2181
```

<210> SEQ ID NO 16
<211> LENGTH: 726
<212> TYPE: PRT
<213> ORGANISM: Chaetomium globosum

<400> SEQUENCE: 16

```
Met Thr Thr Leu Arg Asn Phe Ala Leu Leu Ala Ala Val Leu Ala
 1               5                  10                  15

Arg Val Glu Ala Leu Glu Ala Ala Asp Trp Ala Ala Glu Ala Ser
                20                  25                  30

Ala Lys Thr Ala Leu Ala Lys Met Ser Gln Gln Asp Lys Ile Ser Ile
            35                  40                  45

Val Thr Gly Ile Gly Trp Asp Lys Gly Pro Cys Val Gly Asn Thr Ala
        50                  55                  60

Ala Ile Asn Ser Ile Asn Tyr Pro Gln Leu Cys Leu Gln Asp Gly Pro
65                  70                  75                  80

Leu Gly Ile Arg Phe Gly Thr Gly Ser Thr Ala Phe Thr Pro Gly Val
                85                  90                  95

Gln Ala Ala Ser Thr Trp Asp Thr Glu Leu Met Arg Gln Arg Gly Glu
            100                 105                 110

Tyr Leu Gly Ala Glu Ala Lys Gly Cys Gly Ile His Val Leu Leu Gly
        115                 120                 125

Pro Val Ala Gly Ala Leu Gly Lys Ile Pro His Gly Gly Arg Asn Trp
    130                 135                 140

Glu Gly Phe Gly Thr Asp Pro Tyr Leu Ala Gly Ile Ala Met Ala Glu
145                 150                 155                 160

Thr Ile Glu Gly Leu Gln Ser Ala Gly Val Gln Ala Cys Ala Lys His
                165                 170                 175

Tyr Ile Val Asn Glu Gln Glu Leu Asn Arg Glu Thr Ile Ser Ser Asp
            180                 185                 190

Val Asp Asp Arg Thr Met His Glu Leu Tyr Leu Trp Pro Phe Ala Asp
        195                 200                 205

Ala Val His Ala Asn Val Ala Ser Val Met Cys Ser Tyr Asn Lys Ile
    210                 215                 220

Asn Gly Ser Trp Gly Cys Glu Asn Asp His Ala Gln Asn Gly Leu Leu
225                 230                 235                 240

Lys Lys Glu Leu Gly Phe Lys Gly Tyr Val Val Ser Asp Trp Asn Ala
                245                 250                 255

Gln His Thr Thr Asp Gly Ala Ala Asn Asn Gly Met Asp Met Thr Met
            260                 265                 270

Pro Gly Ser Asp Tyr Asn Gly Asn Val Leu Trp Gly Pro Gln Leu
        275                 280                 285

Ser Asn Ala Val Asn Ser Asn Arg Val Ser Arg Asp Arg Leu Asp Asp
    290                 295                 300

Met Ala Lys Arg Ile Leu Thr Ser Trp Tyr Leu Leu Gly Gln Asn Ser
```

-continued

```
            305                 310                 315                 320
Gly Tyr Pro Asn Ile Asn Ile Asn Ala Asn Val Gln Gly Asn His Lys
                325                 330                 335
Glu Asn Val Arg Ala Val Ala Arg Asp Gly Ile Val Leu Leu Lys Asn
                340                 345                 350
Asp Glu Gly Val Leu Pro Leu Lys Lys Pro Gly Lys Val Ala Leu Val
                355                 360                 365
Gly Ser Ala Ala Ser Val Asn Ser Ala Gly Pro Asn Ala Cys Val Asp
370                 375                 380
Lys Gly Cys Asn Thr Gly Ala Leu Gly Met Gly Trp Gly Ser Gly Ser
385                 390                 395                 400
Val Asn Tyr Pro Tyr Phe Val Ala Pro Tyr Asp Ala Leu Lys Thr Arg
                405                 410                 415
Ala Gln Ala Asp Gly Thr Thr Leu Ser Leu His Asn Ser Asp Ser Thr
                420                 425                 430
Asn Gly Val Ser Gly Val Val Ser Gly Ala Asp Val Ala Ile Val Val
                435                 440                 445
Ile Thr Ala Asp Ser Gly Glu Gly Tyr Ile Thr Val Glu Gly His Ala
                450                 455                 460
Gly Asp Arg Asn His Leu Asp Pro Trp His Asp Gly Asn Ala Leu Val
465                 470                 475                 480
Lys Ala Val Ala Ala Asn Lys Asn Thr Ile Val Val His Ser
                485                 490                 495
Thr Gly Pro Ile Ile Leu Glu Thr Ile Leu Ala Thr Glu Gly Val Lys
                500                 505                 510
Ala Val Val Trp Ala Gly Leu Pro Ser Gln Glu Asn Gly Asn Ala Leu
                515                 520                 525
Val Asp Val Leu Tyr Gly Leu Thr Ser Pro Ser Gly Lys Leu Val Tyr
                530                 535                 540
Ser Ile Ala Lys Arg Pro Glu Asp Tyr Gly Thr Ala Pro Ser Lys Gly
545                 550                 555                 560
Ser Asn Asp Lys Phe Thr Glu Gly Leu Phe Val Asp Tyr Arg His Phe
                565                 570                 575
Asp Asn Ala Lys Ile Glu Pro Arg Tyr Glu Phe Gly Phe Gly Leu Ser
                580                 585                 590
Tyr Thr Glu Phe Thr Tyr Ala Asp Leu Ser Val Thr Ser Thr Val Thr
                595                 600                 605
Ala Gly Pro Ala Ser Gly Glu Thr Ile Pro Gly Gly Ala Ala Asp Leu
                610                 615                 620
Trp Glu Thr Val Ala Thr Val Thr Ala Ser Ile Thr Asn Ser Gly Glu
625                 630                 635                 640
Val Glu Gly Ala Glu Val Ala Gln Leu Tyr Ile Thr Leu Pro Ser Ala
                645                 650                 655
Ala Pro Ser Thr Pro Pro Lys Gln Leu Arg Gly Phe Ala Lys Leu Lys
                660                 665                 670
Leu Glu Pro Gly Ala Ser Gly Val Ala Thr Phe Asn Leu Arg Arg Arg
                675                 680                 685
Asp Leu Ser Tyr Trp Asp Ala Gly Arg Gly Gln Trp Val Val Pro Ala
                690                 695                 700
Gly Glu Phe Thr Val Ser Val Gly Ala Ser Ser Arg Asp Val Arg Leu
705                 710                 715                 720
Thr Gly Ser Leu Thr Ala
                725
```

<210> SEQ ID NO 17
<211> LENGTH: 2208
<212> TYPE: DNA
<213> ORGANISM: Neurospora crassa

<400> SEQUENCE: 17

| | | | | | |
|---|---|---|---|---|---|
| atgcaccttc | gaatatttgc | ggtgttggcc | gcgacttccc | tcgcctgggc | cgagactagc | 60 |
| gagaaacaag | ctcgtcaagc | tggctcaggt | tttgcggcgt | gggacgcagc | ctattctcag | 120 |
| gcaagcactg | ctctctccaa | gctttcacag | caagacaagg | tcaacatcgt | caccggagtc | 180 |
| ggctggaata | agggcccatg | tgttggcaac | accccagcta | ttgcatcaat | cggttatccc | 240 |
| cagctctgtt | tacaagacgg | ccctctcggc | attcggtttg | gaggaagtgt | caccgcgttc | 300 |
| acgcctggta | tccaggcggc | ttcaacatgg | gacgtcgaac | tgattcgaca | gcgcggcgtc | 360 |
| tacctcggtg | cagaagccag | aggggttggc | gtacatgtcc | ttcttggacc | cgtggccgga | 420 |
| gcgcttggca | agatcccaa | tggtggacgt | aactgggagg | gctttggtcc | ggatccctac | 480 |
| ctcacaggta | ttgccatgag | cgaaacaatt | gaagggatcc | agagcaatgg | tgtacaagct | 540 |
| tgcgccaagc | acttcattct | caacgaacag | agagacaaac | cgcgatactat | cagcagtgtc | 600 |
| gtcgacgacc | gcaccatgca | tgaactatac | ctcttccctt | ttgccgatgc | cgtacactca | 660 |
| aatgttgcaa | gtgtgatgtg | cagctacaac | aaggtcaacg | gtacgtgggc | atgtgagaat | 720 |
| gacaaaatcc | agaatggcct | tctcaagaaa | gagctaggct | tcaaaggata | tgtcatgagt | 780 |
| gattggaacg | cccagcacac | cacgaacggc | gctgcaaaca | gtggtatgga | tatgacgatg | 840 |
| ccaggcagtg | actttaatgg | caagacgatc | ctgtggggac | cacagctcaa | caccgccgtc | 900 |
| aacaatggcc | aggtctccaa | agcaagactg | gacgacatgg | ccaagcgcat | tctcgcatcg | 960 |
| tggtatttac | tcgagcaaaa | ctcaggctac | cctgcgacta | acctcaaggc | caatgttcaa | 1020 |
| ggaaaccaca | aggagaacgt | tcgcgcagtg | gcaagagacg | gcattgttct | gctgaagaac | 1080 |
| gacgataaca | tcctcccgct | caagaagcct | agcaagctgg | caatcattgg | gtcatcgtcc | 1140 |
| gttgtcaacc | ctgcgggaag | gaacgcctgc | accgatcgag | gatgcaacac | cggtgcgctc | 1200 |
| ggcatgggtt | ggggctccgg | cacggccgat | taccctact | tcgtagcacc | ctatgatgct | 1260 |
| ctcaagacgc | gggctcagtc | cgacggaaca | actgtcaacc | tactcagctc | tgacagcacc | 1320 |
| agcggcgtag | ccaacgctgc | ctccggagcc | gacgcggcac | tagtcttcat | cacagccgat | 1380 |
| tccggcgaag | gctacatcac | ggtcgagggc | gtgaccggcg | accgtcccaa | cctcgatccc | 1440 |
| tggcacaacg | gcaaccagct | agtccaagcc | gtggctcaag | ccaacaagaa | caccattgtc | 1500 |
| gtcgtccaca | gtaccggccc | catcattctg | gagactatcc | tcgcgcagcc | gggcgtcaag | 1560 |
| gcggtcgtgt | gggccggtct | ccccagccaa | gagaacggca | acgcccttgt | cgatgtccta | 1620 |
| tacggcttgg | tctctcccctc | gggtaagctg | ccgtatacta | tcgccaagag | cgaaagcgac | 1680 |
| tacggcactg | ccgtgcaaag | ggggagggacg | gatctgttca | ctgagggtct | gttcatcgat | 1740 |
| taccgccact | ttgacaagaa | cggtatcgct | ccccggtatg | agttcggttt | cggtctttcc | 1800 |
| tacacgaact | tcacctactc | ctccctctcc | atcacctcca | ccgcctcctc | cggtcccgcc | 1860 |
| tcgggtgaca | ccatccctgg | cggccgcgcc | gacctctggg | aaaccgtggc | aaccgtcact | 1920 |
| gccgtcgtca | aaaacacggg | tggtgtgcag | ggcgccgagg | caccccagct | atacatcacc | 1980 |
| ttgccctctt | ccgcgccgtc | gagcccgccg | aaacagctca | gagggtttgc | aaagctgaag | 2040 |
| ctggcgcccg | gggagagcaa | gacagctacg | ttcattttgc | ggaggaggga | tttgagttat | 2100 |

```
tgggatacgg gcagccagaa ttgggtggtg cctagtggca gctttgtggt ggtagtgggt    2160
gctagttcga gggatttgag gttgaatggg aagtttgatg tttattga                2208
```

<210> SEQ ID NO 18
<211> LENGTH: 735
<212> TYPE: PRT
<213> ORGANISM: Neurospora crassa

<400> SEQUENCE: 18

```
Met His Leu Arg Ile Phe Ala Val Leu Ala Ala Thr Ser Leu Ala Trp
1               5                   10                  15

Ala Glu Thr Ser Glu Lys Gln Ala Arg Gln Ala Gly Ser Gly Phe Ala
                20                  25                  30

Ala Trp Asp Ala Ala Tyr Ser Gln Ala Ser Thr Ala Leu Ser Lys Leu
            35                  40                  45

Ser Gln Gln Asp Lys Val Asn Ile Val Thr Gly Val Gly Trp Asn Lys
        50                  55                  60

Gly Pro Cys Val Gly Asn Thr Pro Ala Ile Ala Ser Ile Gly Tyr Pro
65                  70                  75                  80

Gln Leu Cys Leu Gln Asp Gly Pro Leu Gly Ile Arg Phe Gly Gly Ser
                85                  90                  95

Val Thr Ala Phe Thr Pro Gly Ile Gln Ala Ala Ser Thr Trp Asp Val
            100                 105                 110

Glu Leu Ile Arg Gln Arg Gly Val Tyr Leu Gly Ala Glu Ala Arg Gly
        115                 120                 125

Val Gly Val His Val Leu Leu Gly Pro Val Ala Gly Ala Leu Gly Lys
    130                 135                 140

Ile Pro Asn Gly Gly Arg Asn Trp Glu Gly Phe Gly Pro Asp Pro Tyr
145                 150                 155                 160

Leu Thr Gly Ile Ala Met Ser Glu Thr Ile Glu Gly Ile Gln Ser Asn
                165                 170                 175

Gly Val Gln Ala Cys Ala Lys His Phe Ile Leu Asn Glu Gln Glu Thr
            180                 185                 190

Asn Arg Asp Thr Ile Ser Ser Val Val Asp Asp Arg Thr Met His Glu
        195                 200                 205

Leu Tyr Leu Phe Pro Phe Ala Asp Ala Val His Ser Asn Val Ala Ser
    210                 215                 220

Val Met Cys Ser Tyr Asn Lys Val Asn Gly Thr Trp Ala Cys Glu Asn
225                 230                 235                 240

Asp Lys Ile Gln Asn Gly Leu Leu Lys Lys Glu Leu Gly Phe Lys Gly
                245                 250                 255

Tyr Val Met Ser Asp Trp Asn Ala Gln His Thr Thr Asn Gly Ala Ala
            260                 265                 270

Asn Ser Gly Met Asp Met Thr Met Pro Gly Ser Asp Phe Asn Gly Lys
        275                 280                 285

Thr Ile Leu Trp Gly Pro Gln Leu Asn Thr Ala Val Asn Asn Gly Gln
    290                 295                 300

Val Ser Lys Ala Arg Leu Asp Asp Met Ala Lys Arg Ile Leu Ala Ser
305                 310                 315                 320

Trp Tyr Leu Leu Glu Gln Asn Ser Gly Tyr Pro Ala Thr Asn Leu Lys
                325                 330                 335

Ala Asn Val Gln Gly Asn His Lys Glu Asn Val Arg Ala Val Ala Arg
            340                 345                 350

Asp Gly Ile Val Leu Leu Lys Asn Asp Asp Asn Ile Leu Pro Leu Lys
```

-continued

```
                355                 360                 365
Lys Pro Ser Lys Leu Ala Ile Ile Gly Ser Ser Val Val Asn Pro
            370                 375                 380

Ala Gly Arg Asn Ala Cys Thr Asp Arg Gly Cys Asn Thr Gly Ala Leu
385                 390                 395                 400

Gly Met Gly Trp Gly Ser Gly Thr Ala Asp Tyr Pro Tyr Phe Val Ala
                405                 410                 415

Pro Tyr Asp Ala Leu Lys Thr Arg Ala Gln Ser Asp Gly Thr Thr Val
            420                 425                 430

Asn Leu Leu Ser Ser Asp Ser Thr Ser Gly Val Ala Asn Ala Ala Ser
            435                 440                 445

Gly Ala Asp Ala Ala Leu Val Phe Ile Thr Ala Asp Ser Gly Glu Gly
            450                 455                 460

Tyr Ile Thr Val Glu Gly Val Thr Gly Asp Arg Pro Asn Leu Asp Pro
465                 470                 475                 480

Trp His Asn Gly Asn Gln Leu Val Gln Ala Val Ala Gln Ala Asn Lys
                485                 490                 495

Asn Thr Ile Val Val His Ser Thr Gly Pro Ile Ile Leu Glu Thr
            500                 505                 510

Ile Leu Ala Gln Pro Gly Val Lys Ala Val Trp Ala Gly Leu Pro
            515                 520                 525

Ser Gln Glu Asn Gly Asn Ala Leu Val Asp Val Leu Tyr Gly Leu Val
            530                 535                 540

Ser Pro Ser Gly Lys Leu Pro Tyr Thr Ile Ala Lys Ser Glu Ser Asp
545                 550                 555                 560

Tyr Gly Thr Ala Val Gln Arg Gly Gly Thr Asp Leu Phe Thr Glu Gly
                565                 570                 575

Leu Phe Ile Asp Tyr Arg His Phe Asp Lys Asn Gly Ile Ala Pro Arg
            580                 585                 590

Tyr Glu Phe Gly Phe Gly Leu Ser Tyr Thr Asn Phe Thr Tyr Ser Ser
            595                 600                 605

Leu Ser Ile Thr Ser Thr Ala Ser Ser Gly Pro Ala Ser Gly Asp Thr
            610                 615                 620

Ile Pro Gly Gly Arg Ala Asp Leu Trp Glu Thr Val Ala Thr Val Thr
625                 630                 635                 640

Ala Val Val Lys Asn Thr Gly Gly Val Gln Gly Ala Glu Ala Pro Gln
                645                 650                 655

Leu Tyr Ile Thr Leu Pro Ser Ser Ala Pro Ser Ser Pro Lys Gln
            660                 665                 670

Leu Arg Gly Phe Ala Lys Leu Lys Leu Ala Pro Gly Glu Ser Lys Thr
            675                 680                 685

Ala Thr Phe Ile Leu Arg Arg Arg Asp Leu Ser Tyr Trp Asp Thr Gly
            690                 695                 700

Ser Gln Asn Trp Val Val Pro Ser Gly Ser Phe Gly Val Val Val Gly
705                 710                 715                 720

Ala Ser Ser Arg Asp Leu Arg Leu Asn Gly Lys Phe Asp Val Tyr
                725                 730                 735
```

BETA-GLUCOSIDASE VARIANTS HAVING IMPROVED ACTIVITY, AND USES THEREOF

The present invention relates to the expression and optimization of enzymes involved in lignocellulosic biomass decomposition. The present invention relates more particularly to beta-glucosidase variants comprising at least one modification among the amino acids located at positions 225, 238, 240 and 241, according to the numbering in SEQ ID No. 2, of the beta-glucosidase of *Trichoderma reesei*, and also to the use of these variants with improved effectiveness in methods for cellulose decomposition and methods for producing biofuel (for example: ethanol, butanol, isopropanol).

The possibility of producing ethanol from cellulose has received a great deal of attention owing to the availability of large amounts of starting material and also to the cleanliness of ethanol as a fuel.

The natural cellulosic starting materials for such a process are denoted using the term "biomass". Many types of biomass, including wood, agricultural residues, herbaceous crops and solid municipal waste, have been considered as starting materials for biofuel production. These materials are constituted mainly of cellulose, hemicellulose and lignin.

Cellulose is a polymer constituted of glucose molecules linked by beta 1-4 linkages, which is very resistant to decomposition or to depolymerization using acids, enzymes or microorganisms. Once the cellulose has been converted to glucose, said glucose is easily fermented to biofuel, for example ethanol, using a yeast.

The oldest methods studied for converting cellulose to glucose are based on acid hydrolysis. This process can be carried out in the presence of acid concentrates or dilute acids. However, several drawbacks, such as poor recovery of the acid when acid concentrates are used and low glucose production in the case of the use of dilute acids, prevent the acid hydrolysis process from reaching commercialization.

In order to overcome the drawbacks of the acid hydrolysis process, cellulose conversion processes have more recently involved enzymatic hydrolysis, using cellulose-type enzymes. This enzymatic hydrolysis of the lignocellulosic biomass (for example, cellulose) has, however, the drawback of being an expensive industrial process. As a result, it is necessary to use strains of microorganisms that secrete cellulases which are increasingly effective.

In this respect, many microorganisms contain enzymes which hydrolyze cellulose, such as the fungi *Trichoderma*, *Aspergillus*, *Humicola* or *Fusarium* and also bacteria such as *Thermomonospora*, *Bacillus*, *Cellulomonas* and *Streptomyces*. The enzymes present in these microorganisms have three types of activities that are of use in the conversion of cellulose to glucose and can be divided up into three groups: endoglucanases, which attack cellulose fibers randomly internally, exoglucanases, which will attack the ends of the fibers, releasing cellobiose therefrom, and beta-glucosidases, which will hydrolyze this cellobiose to glucose. These beta-glucosidases constitute the limiting step of the method for cellulose conversion. This is because the primary difficulty of the method lies in the conversion of the cellobiose to glucose, since any cellobiose not hydrolyzed at the end of the method represents a loss of yield during the production of biofuel.

This accumulation of cellobiose is a major problem in enzymatic hydrolysis, given that several microorganisms which produce cellulases, including *Trichoderma*, produce very little beta-glucosidase. Specifically, less than 1% of the total proteins produced by industrial *Trichoderma* strains are of beta-glucosidase type. This low amount of beta-glucosidase therefore results in a low capacity for hydrolyzing cellobiose to glucose, hence the accumulation of said cellobiose in the system. Moreover, a high concentration of cellobiose inhibits the activity of the other cellulases, and in particular the exoglucanases, for which cellobiose is the final reaction product.

Several approaches have been proposed for increasing the beta-glucosidase activity in the microorganisms and, consequently, the conversion of the cellobiose to glucose.

A first approach consists in adding exogenously produced beta-glucosidase to the mixtures secreted by the microorganisms, in order to improve the hydrolysis. However, this method is not commercially viable since it is much too expensive.

A second approach, as described in WO 92/010581, is to use genetic engineering to insert new copies of the beta-glucosidase gene into the genome of the microorganisms, in such a way that said microorganisms produce a larger amount of enzyme.

A third approach, described in WO 99/46362, consists in genetically modifying the microorganisms using a genetic construct which comprises a promoter, the mature beta-glucosidase gene and the xylanase secretion signal sequence. The presence of the xylanase secretion signal sequence makes it possible to significantly increase the amount of beta-glucosidase produced by the microorganisms.

However, in order for a hydrolysis of the lignocellulosic biomass to be effective and economically profitable, the enzymatic mixture must be produced by a one and only microbial strain, and must comprise balanced proportions of various enzymatic activities (inter alia, but not exclusively, exoglucanases, endoglucanases, xylanases and beta-glucosidases). By way of example, in the natural mixtures of *Trichoderma reesei*, the presence of 70-80% of exoglucanases, 15-20% of endoglucanases, a few percent of hemicellulases and approximately 0.5% of beta-glucosidases is generally noted. This mixture is perfectly suitable for hydrolyzing the majority of pretreated substrates (for example, such as wheat straw which has been steam-exploded under acid conditions) with acceptable yields. In summary, if the increase in beta-glucosidase activity is carried out by enrichment of the amount of enzyme, this must not be done to the detriment of the other enzymatic activities.

Consequently, the possibility of obtaining high beta-glucosidase activities without notably modifying the proportion of all the enzymes of the mixture would be a significant gain for the method for converting lignocellulosic biomass to biofuel.

With this perspective, the applicant companies have, to their great credit, found, after a great deal of research, an isolated or purified polypeptide having an improved beta-glucosidase activity compared with the beta-glucosidase activity of the wild-type BGL1 protein (SEQ ID No. 2), comprising an amino acid sequence in which at least one amino acid is modified compared with the amino acid sequence according to SEQ ID No. 2, said modified amino acid being chosen from positions 225, 238, 240 and 241 of the amino acid sequence SEQ ID No. 2, and said amino acid sequence having at least 75% sequence identity with SEQ ID No. 2 and preferably at least 80%, 85%, 90%, 95%, 97%, 98%, 99% sequence identity with SEQ ID No. 2.

Furthermore, the polypeptides according to the invention have the advantage of being less sensitive to inhibition by glucose and, as a result, maintain a better beta-glucosidase activity in the presence of a high glucose concentration.

In one embodiment, the polypeptide as described above is characterized in that it has a beta-glucosidase activity determined in the presence of glucose which is improved compared with the beta-glucosidase activity of the wild-type BGL1 protein (SEQ ID No. 2) determined in the absence of glucose.

Those skilled in the art may, for example, determine the increase or, in other words, the improvement in the enzymatic activity of a polypeptide according to the invention by means of an enzymatic activity test using the substrate pnp-glucopyranoside. The amount of para-nitrophenol obtained after action of the beta-glucosidase may, for example, be determined by reading the optical density at 414 nm.

An example of a protocol, that those skilled in the art may use to determine whether a polypeptide according to the invention has an improved enzymatic activity compared with that of the wild-type BGL1 protein, is the following:
- formation of a stock culture of *E. coli* expressing a polypeptide according to the invention, overnight at 37° C.;
- inoculation of an LB culture medium with 1% of stock culture for 24 h at 20° C.;
- centrifugation for 2 minutes at 13 000 rpm;
- resuspension of the cell pellets with 100 mM succinate buffer at pH 5 (final $OD_{600}$ of 100);
- incubation of 50 µl of cells with 100 µl of 100 mM succinate buffer, at pH 5, containing 15 mM of pnp-glucopyranoside for 1 h 30 at 50° C., followed by 5 minutes on ice;
- addition of 150 µl of 0.2 M $Na_2CO_3$;
- centrifugation for 2 minutes at 13 000 rpm;
- reading of the optical density at 414 nm on 150 µl of supernatant.

In addition, those skilled in the art may use the protocol described above, incubating the 50 µl of cells with 100 µl of 100 mM succinate buffer, at pH 5, containing 15 mM of pnp-glucopyranoside and 60 g/l of glucose for 1 h 30 at 50° C., in order to determine whether a polypeptide according to the invention is less sensitive to inhibition by glucose than the wild-type BGL1 protein.

In the context of the invention, a "modified" amino acid means a "substituted", "inserted" or "deleted" amino acid.

According to one embodiment, the "modified" amino acid is "substituted" compared with the amino acid sequence according to SEQ ID No. 2.

According to one embodiment, the "modified" amino acid is "inserted" compared with the amino acid sequence according to SEQ ID No. 2.

According to one embodiment, the "modified" amino acid is "deleted" compared with the amino acid sequence according to SEQ ID No. 2.

According to one embodiment, the polypeptide as described above is characterized in that at least two amino acids of the amino acid sequence are modified compared with the amino acid sequence SEQ ID No. 2, said modified amino acids being chosen from positions 225, 238, 240 and 241 of the sequence SEQ ID No. 2.

According to one embodiment, the polypeptide as described above is characterized in that at least three amino acids of the amino acid sequence are modified compared with the amino acid sequence SEQ ID No. 2, said modified amino acids being chosen from positions 225, 238, 240 and 241 of the amino acid sequence SEQ ID No. 2.

According to one embodiment, the polypeptide as described above is characterized in that at least four amino acids of the amino acid sequence are modified compared with the amino acid sequence SEQ ID No. 2, said modified amino acids being those of positions 225, 238, 240 and 241 of the amino acid sequence SEQ ID No. 2.

According to one embodiment, the polypeptide as described above is characterized in that at least one, at least two, at least three or at least four amino acids of the amino acid sequence are modified compared with the amino acid sequence SEQ ID No. 2, said modifications being chosen from Q225H, V238I, T240G and T241S.

According to one embodiment, the polypeptide as described above is characterized in that one amino acid is modified compared with the sequence SEQ ID No. 2, said modification being Q225H.

According to one embodiment, the polypeptide as described above is characterized in that three amino acids are modified compared with the sequence SEQ ID No. 2, said modifications being V238I, T240G and T241S.

According to one embodiment, the polypeptide as described above is characterized in that four amino acids are modified compared with the sequence SEQ ID No. 2, said modifications being Q225H, V238I, T240G and T241S.

According to one embodiment, the polypeptide as described above also comprises at least one additional modified amino acid chosen from positions 97, 99, 100, 118, 119, 121, 123, 126, 127, 128, 130, 132, 134, 135, 140, 147, 151, 153, 163, 168, 173, 174, 177, 179, 182, 187, 193, 206, 207, 212, 217 and 621 of the amino acid sequence SEQ ID No. 2.

According to one embodiment, the polypeptide as described above is characterized in that said additional modified amino acid comprises one or more modifications selected from the group consisting of V97I, Y99F, S100G, V118T, N119E, I121M, E123Q, Q126E, F127Y, I128L, E130A, V132A, A134G, S135C, S135V, I140L, P147A, T151I, Q153H, V163T, T168A, G173A, G173S, Q174E, N177E, I179L, V182A, V182N, I187C, L193V, N206D, P207V, L212M, T217L, L621F and L621T.

According to one embodiment, the polypeptide as described above is selected from the group consisting of:
- an amino acid sequence chosen from SEQ ID No. 4, SEQ ID No. 6, SEQ ID No. 8, SEQ ID No. 10, SEQ ID No. 12, SEQ ID No. 14; or
- an amino acid sequence SEQ ID No. X having:
  i) a percentage of identical residues relative to the length of SEQ ID No. 4, 6, 8, 10, 12 or 14 of at least 70% identity, preferably 75%, 80%, 85%, 90%, 95%, 98% or 99%;
  ii) a percentage of identical residues relative to the length of SEQ ID No. X of at least 70% identity, preferably 75%, 80%, 85%, 90%, 95%, 98% or 99%.

Variants of the amino acid sequences of the present invention can be prepared by various conventional methods, such as random mutagenesis, site-directed mutagenesis, gene synthesis or shuffling, using all or a part of the nucleotide or peptide sequences presented in the present text. Such variants comprise, for example, deletions and/or insertions and/or substitutions of residues in the amino acid sequence of the enzyme. The present invention relates to any variant obtained from the sequences presented in this text, provided that the variants of said amino acid sequences retain an improved beta-glucosidase function (as defined above) compared with Bgl-1.

In one embodiment, the invention relates to an amino acid sequence, hereinafter referred to, for practical reasons, as SEQ ID No. X, which, when aligned with SEQ ID No. 4, 6, 8, 10, 12 or 14, comprises:
a) a percentage of identical residues relative to the length of SEQ ID No. 4, 6, 8, 10, 12 or 14 of at least 70% identity, preferably 75%, 80%, 85%, 90%, 95%, 98% or 99%; and b) a percentage of identical residues relative to the length of SEQ ID No. X of at least 70% identity, preferably 75%, 80%, 85%, 90%, 95%, 98% or 99%.

According to the invention, the percentage of identical residues relative to the length of SEQ ID No. 4, 6, 8, 10, 12 or 14 corresponds to the number of residues that are identical between SEQ ID No. X and SEQ ID No. 4, 6, 8, 10, 12 or 14, divided by the number of residues in SEQ ID No. 4, 6, 8, 10, 12 or 14. When using the GenomeQuest database, said percentages of identical residues relative to the length of SEQ ID No. 4, 6, 8, 10, or 14 correspond to Query percentage identities (% id Query), where Query corresponds to the sequence SEQ ID No. 4, 6, 8, 10, 12 or 14.

According to the invention, the percentage of identical residues relative to the length of SEQ ID No. X corresponds to the number of residues that are identical between SEQ ID No. X and SEQ ID No. 4, 6, 8, 10, 12 or 14, divided by the number of residues in SEQ ID No. X. When using the GenomeQuest database, said percentages of identical residues relative to the length of SEQ ID No. X correspond to Subject percentage identities (% id Subject), where Subject corresponds to SEQ ID No. X.

The subject of the invention is also a purified or isolated nucleic acid encoding at least one polypeptide as described above. Table 1 below comprises the identifications of the nucleic and peptide sequences for the Bgl-1 genes and the genes A and C, and also for the polypeptides of the invention.

TABLE 1

| Clones | Nucleic acid | Polypeptide |
| --- | --- | --- |
| BGL1 (wild-type) | SEQ ID No. 1 | SEQ ID No. 2 |
| 10H7 | SEQ ID No. 3 | SEQ ID No. 4 |
| 59B8 | SEQ ID No. 5 | SEQ ID No. 6 |
| 164A2 | SEQ ID No. 7 | SEQ ID No. 8 |
| 100B11 | SEQ ID No. 9 | SEQ ID No. 10 |
| 115E1 | SEQ ID No. 11 | SEQ ID No. 12 |
| 149G7 | SEQ ID No. 13 | SEQ ID No. 14 |
| Gene A | SEQ ID No. 15 | SEQ ID No. 16 |
| Gene C | SEQ ID No. 17 | SEQ ID No. 18 |

The invention also relates to a vector comprising a nucleic acid as described above.

According to the invention, the term "vector" is intended to mean any DNA sequence into which it is possible to insert fragments of foreign nucleic acid, the vectors making it possible to introduce foreign DNA into a host cell. Examples of vectors are plasmids, cosmids, yeast artificial chromosomes (YACs), bacterial artificial chromosomes (BACs) and P1 bacteriophage-derived artificial chromosomes (PACs), and virus-derived vectors.

According to the invention, the nucleic acid as described above may be functionally linked to a promoter, a terminator or any other sequence necessary for the expression of said nucleic acid in the host cell.

The vector according to the invention may also carry a selectable marker. The term "selectable marker" is intended to mean a gene, the expression of which confers, on the cells which contain it, a characteristic which makes it possible to select said cells. It is, for example, an antibiotic resistance gene.

The subject of the invention is also an isolated host cell comprising either at least one of the polypeptides as described above, or at least one of the nucleic acids as described above, or at least one of the vectors as described above.

Those skilled in the art may introduce at least one of the polypeptides, at least one of the nucleic acids or at least one of the vectors as described above into the host cell by well-known conventional means. For example, mention may be made of calcium chloride treatment, electroporation, or the use of a particle gun.

According to one embodiment, those skilled in the art may introduce into the host cell, and by conventional means, several copies of a nucleic acid encoding a polypeptide having an improved beta-glucosidase activity according to the invention.

According to one embodiment, the isolated host cell as described above is chosen from *Trichoderma, Aspergillus, Neurospora, Humicola, Penicillium, Fusarium, Thermomonospora, Bacillus, Pseudomonas, Escherichia, Clostridium, Cellulomonas, Streptomyces, Yarrowia, Pichia* and *Saccharomyces*.

According to one preferred embodiment, the isolated host cell as described above is chosen from *Trichoderma reesei, Trichoderma viridae, Trichoderma koningii, Aspergillus niger, Aspergillus nidulans, Aspergillus wentii, Aspergillus oryzae, Aspergillus phoenicis, Neurospora crassa, Humicola grisae, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca* and mixtures thereof.

According to one preferred embodiment, the isolated host cell as described above is *Trichoderma reesei*.

The invention also relates to the use of any one of the polypeptides described above, for the hydrolysis of beta-oligosaccharides.

The invention also relates to the use of any one of the polypeptides described above, for the hydrolysis of cellobiose to glucose.

The subject of the invention is also the use of any one of the polypeptides described above, for the production of biofuel.

According to the invention, the term "biofuel" can be defined as any product which results from biomass conversion and which can be used for energy purposes. Furthermore, and without wanting to be limited, mention may be made, by way of example, of biogases, products that can be incorporated (optionally after subsequent conversion) into a fuel or that can be a fuel in their own right, such as alcohols (ethanol, butanol and/or isopropanol according to the type of fermentative organism used), solvents (acetone), acids (butyric acid), lipids and derivatives thereof (short-chain or long-chain fatty acids, fatty acid esters), and also hydrogen.

Preferably, the biofuel according to the invention is an alcohol, for example ethanol, butanol and/or isopropanol. More preferably, the biofuel according to the invention is ethanol.

In another embodiment, the biofuel is biogas.

In addition to the production of biofuel, the polypeptides having an improved beta-glucosidase activity according to the invention can also be used in other types of applications by catalyzing the hydrolysis of various substrates, thus allowing the release of a variety of flavors. By way of example, they can be used in order to release fruit flavors by catalyzing several glucosides present inside these fruits or, alternatively, they can hydrolyze the monoterphenyl beta-glucosidases of grapes, thus representing an important source of flavors for wine. Consequently, the polypeptides having an improved beta-glucosidase activity according to the invention can be used in several fields, in particular in perfumery, in the food industry, in enology, etc.

The strains of filamentous fungi, preferably *Trichoderma*, more preferably *T. reesei*, capable of expressing at least one polypeptide according to the invention are cultured in fermenters, in the presence of a carbon-based substrate, such as lactose or glucose, chosen for the growth of the microorganism. In one embodiment, this carbon-based substrate, depending on its nature, is introduced into the fermenter before sterilization or is sterilized separately and introduced into the fermenter after sterilization of the latter, so as to obtain an initial concentration of 20 to 35 g/l.

An aqueous solution containing the substrate chosen for the production of the enzymes is then added. An enzymatic composition which acts on lignocellulosic biomass, produced by the fungi, is finally recovered by filtration of the culture medium. This composition contains in particular endoglucanase, exoglucanase and the beta-glucosidase according to the invention. In one embodiment, the aqueous solution containing the substrate chosen for the production of the enzymes is prepared at the concentration of 200-250 g/l; this solution should contain the inducing substrate such as lactose. This aqueous solution is injected after exhaustion of the initial carbon-based substrate so as to provide an optimized amount, of between 35 and 45 mg/g of cells ("fed batch"). During this "fed batch" phase, the residual sugar concentration in the culture medium is less than 1 g/l and the enzymes which act on lignocellulosic biomass are secreted by the fungus. Said enzymes can be recovered by filtration of the culture medium.

The subject of the invention is an enzymatic composition which acts on lignocellulosic biomass, said enzymatic composition being produced by filamentous fungi and comprising at least one polypeptide having an improved beta-glucosidase activity compared with the beta-glucosidase activity of the wild-type BGL1 protein.

Finally, the subject of the invention is a method for producing biofuel from biomass, comprising the following steps:
suspending in an aqueous phase the material to be hydrolyzed;
adding an enzymatic composition which acts on lignocellulosic biomass, as described above;
assaying the sugars released;
separating the sugar solution from the nonhydrolyzed solid fraction;
fermenting the sugar solution;
separating the biofuel from the fermentation must.

In one embodiment, the material to be hydrolyzed is suspended in an aqueous phase in a proportion of from 6% to 40% of dry matter, preferably 20% to 30%. The pH is adjusted to between 4 and 5.5, preferably between 4.8 and 5.2, and the temperature is adjusted to between 40 and 60° C., preferably between 45 and 50° C. The hydrolysis reaction is initiated by adding the enzymatic composition which acts on lignocellulosic biomass; the amount normally used is from 10 to 30 mg of excreted proteins per gram of pretreated substrate or less. The reaction generally lasts from 15 to 48 hours. The reaction is followed by assaying the sugars released, in particular the glucose. The sugar solution is separated from the nonhydrolyzed solid fraction, essentially constituted of lignin, by filtration or centrifugation; it is used for the fermentation.

In one embodiment, the biofuel may be separated from the fermentation must by distillation.

Another subject of the invention is a method for producing biofuel from biomass, characterized in that it comprises the following steps:
suspending in an aqueous phase the biomass to be hydrolyzed;
simultaneously adding an enzymatic composition which acts on lignocellulosic biomass, as defined above, and a fermentative organism;
separating the biofuel from the fermentation must.

According to this embodiment, the cellulose present in the biomass is converted to glucose, and at the same time, in the same reactor, the fermentative organism (for example a yeast) converts the glucose to final product according to an SSF (simultaneous saccharification and fermentation) process known to those skilled in the art. Depending on the metabolic and hydrolytic capacities of the fermentative organism, the addition of a more or less large amount of exogenous cellulolytic mixture may be required in order for the operation to run smoothly.

In another embodiment, one and the same fermentative organism may be capable of converting the biomass to glucose and then the glucose to final product.

The use of the polypeptide having a better beta-glucosidase activity according to the present invention thus provides the advantage of obtaining a better glucose production yield. The present invention thus makes it possible to use less enzyme than previously, which provides an economic advantage, the production cost of the biofuel, for example, being lower.

Other aspects, subjects, advantages and characteristics of the invention will be presented on reading the nonrestrictive description which follows and which describes preferred embodiments of the invention given by means of examples and of FIG. 1.

EXAMPLES

Example 1

1st Round of Shuffling

Figure 1:
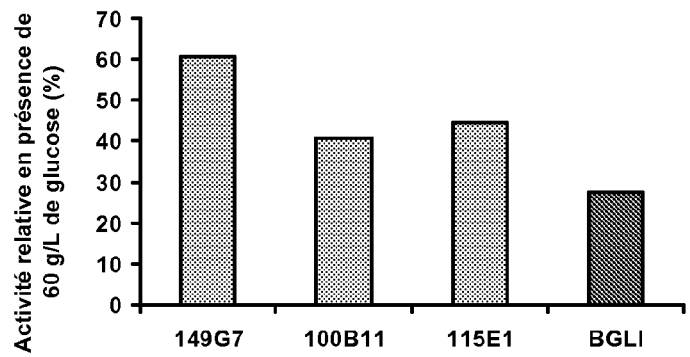
FIG. 1 is a graph representing the improvement in the beta-glucosidase activity for the variants 149G7, 100B11 and 115E1 in comparison with the parent BGL1 gene, when in the presence of glucose.

The sequence of the *Trichoderma reesei* beta-glucosidase gene (parental BGL1 gene, SEQ ID No. 1) was subjected to a first round of shuffling according to the patented method described in EP 1104457B1 with the putative glucosidase gene of *Chaetomium globosum* (gene A) (SEQ ID No. 15 and SEQ ID No. 16 (protein sequence)) having 70% identity with the parental BGL1 gene.

1—High-throughput Screening

A high-throughput screening test made it possible to select the best clones resulting from the shuffling of these two sequences, i.e. those having an improvement factor greater than 2 in terms of the beta-glucosidase activity when compared with the parental BGL1 gene of *T. reesei*.

The tests for screening of the library of the first round of shuffling was carried out according to the following steps:
isolation on agar of the various colonies of *E. coli* expressing the shuffling variants for the recombinant enzyme according to the invention and preculturing of said colonies in LB medium overnight at 37° C.;
inoculation of an LB medium at 3% with the preculture, then incubation for 4 h at 37° C.;
induction of the expression of the variants by addition of 100 µM isopropyl-beta-thiogalactoside (IPTG), then incubation at 20° C. overnight;
centrifugation for 2 minutes at 13 000 rpm;
resuspension of the cell pellets in 100 µL of 0.1M succinate buffer containing 2.2 mM of para-nitrophenyl-D-glucoside-6-phosphate (pNPGlc);
incubation for 3 h at room temperature;
reading of the optical density at 414 nm after alkalinization.

Under these screening conditions, an improvement in the beta-glucosidase activity compared with the BGL1 reference enzyme was found in several clones, including in particular the clones 10H7 (SEQ ID Nos. 3 and 4), 59B8 (SEQ ID Nos. 5 and 6) and 164A2 (SEQ ID Nos. 7 and 8).

2—Determination of the Improvement in the β-glucosidase Activity 2-1/On the Substrate pNPGlc In order to determine the relative kcat of the variants selected in the first round of shuffling, the following procedure is carried out:
formation of a stock culture of *E. coli* expressing a recombinant enzyme according to the invention, overnight at 37° C.;
inoculation of an LB culture medium with 1% of stock culture for 24 h at 20° C. with induction using IPTG (250 µM);
centrifugation for 2 minutes at 13 000 rpm;
resuspension of the cell pellets with 100 mM succinate buffer at pH 5 (final $OD_{600}$ of 100);
incubation of 50 µl of cells with 100 µl of 100 mM succinate buffer at pH 5 containing 15 mM of pnp-glucopyranoside for 1 h 30 at 50° C., followed by 5 minutes on ice;
addition of 150 µl of 0.2M $Na_2CO_3$;
centrifugation for 2 minutes at 13 000 rpm;
reading of the optical density at 414 nm on 150 µl of supernatant.

Table 2 gives the values of the kcats and also the improvement factors obtained for the clones 10H7, 59B8 and 164A2 under these experimental conditions.

TABLE 2

Improvement in beta-glucosidase activity
(results of the induced cultures)

|  | Clones | $K_{cat}$ (min$^{-1}$) | Improvement factor |
| --- | --- | --- | --- |
| 1st round clones | 10H7 | 590.0 | 8 |
|  | 59B8 | 518.6 | 7 |
|  | 164A2 | 1437.3 | 20 |
| reference protein | BGLI | 71.0 | 1 |

The results show very large improvements in enzymatic activities compared with the reference enzyme (BGL1) for the 3 clones 10H7, 59B8 and 164A2.

2-2/On Cellobiose

The improvement in activity of the clones 10H7, 59B8 and 164A2 was then confirmed on a second substrate: cellobiose.

This test was carried out on cultures of *E. coli* expressing a recombinant enzyme according to the invention. The steps of the test are as follows:

Inoculation of an LB culture medium with 1% of stock culture induced with IPTG, then incubation overnight at 37° C.
Culturing of said cells at 37° C. until an optical density at 600 nm of 0.4 is obtained.
Induction of said cells with 250 µM IPTG 250 at 20° C. for 20 hours.
Washing of the cell pellets three times in a 100 mM succinate buffer, pH 5, in order to remove the glucose of the culture medium.
Incubation of 10 µl of said cells with 190 µl of 263.2 mM cellobiose (250 mM final concentration) for 12 hours at 50° C. in a microplate.
Developing:
Mixing and incubation, for 1 h at room temperature, of:
10 µl of above reaction
90 µl of 100 mM succinate buffer at pH 5
5 µl of glucose oxidase, 44 U/ml,
Mixing and incubation, for 30 min at room temperature, of:
10 µl of glucose oxidase reaction
2 µl of horse radish peroxidase at 10 U/ml
5 µl of 100 mM ABTS
83 µl of 50 mM phosphate buffer, pH 7.4,
Reading of the optical densities at 420 nm.

TABLE 3

Improvement in beta-glucosidase activity
(results of the induced cultures)

|  | Clones | $k_{cat}$ (min$^{-1}$) | Improvement factor |
| --- | --- | --- | --- |
| 1st round clones | 10H7 | 69.1 | 13 |
|  | 59B8 | 37.7 | 7 |
|  | 164A2 | 213.2 | 41 |
| reference protein | BGLI | 5.2 | 1 |

Similarly, the results show very large improvements in enzymatic activities compared with the starting enzyme (BGL1) for the clones 10H7, 59B8 and 164A2 where cellobiose is used as substrate.

Example 2

2nd Round of Shuffling

The sequences of the improved genes obtained in the first round of shuffling were subsequently subjected to a second round of shuffling (still according to the patented method described in EP1104457B1). In order to increase the genetic diversity, at least one gene encoding a beta-glucosidase having 70% identity was added. In this specific example, the gene of the putative glucosidase of *Neurospora crassa* (gene C) (SEQ ID No. 17 and SEQ ID No. 18 (protein sequence)) was used.

1—High-throughput Screening

A high-throughput screening test as described previously (with the exception of the IPTG induction step, since the improvement provided in the first round of shuffling allows detection of the beta-glucosidase activity based only on the leakage of the promoter) was carried out on the clones obtained following this second round of shuffling, in order to select the best clones, i.e. those having an improvement factor greater than 2 in terms of the beta-glucosidase activity when compared with the clone 164A2.

Under these screening conditions, an improvement in the beta-glucosidase activity compared with the reference enzyme (164A2) was found in several clones, including in particular the clones 100B11 (SEQ ID Nos. 9 and 10), and 115E1 (SEQ ID Nos. 11 and 12).

2—Determination of the Improvement in the β-glucosidase Activity 2-1/On pNPGlc

In order to determine the relative kcat, the activities of the clones 100B11 and 115E1 were measured using the activity test as described previously.

Table 4 gives the values of the kcats and also the improvement factors obtained for the clones 100B11 and 115E1 under these experimental conditions.

TABLE 4

Improvement in beta-glucosidase activity
(results of the induced cultures)

|  | Clones | $K_{cat}$ (min$^{-1}$) | Improvement factor |
|---|---|---|---|
| 2nd round clones | 100B11 | 4342.8 | 3.0 |
|  | 115E1 | 3989.2 | 2.8 |
| reference protein | 164A2 | 1437.3 | 1 |

The results show very large improvements in enzymatic activities compared with the reference enzyme (164A2) and with (BGL1) (×60) for the clones 100B11 and 115E1.

2-2/On Cellobiose

The improvement in activity of the clones 100B11 and 115E1 was then confirmed on a second substrate: cellobiose.

In order to determine the relative kcat, the activities of the clones 100B11 and 115E1 were measured by means of the activity test as described previously, using cellobiose as substrate.

TABLE 5

Improvement in beta-glucosidase activity
(results of the induced cultures)

|  | Clones | $K_{cat}$ (min$^{-1}$) | Improvement factor |
|---|---|---|---|
| 2nd round clones | 100B11 | 387.2 | 1.8 |
|  | 115E1 | 406.4 | 1.9 |
| reference protein | 164A2 | 213.2 | 1 |

Similarly, the results show large improvements in enzymatic activities compared with the reference enzyme (164A2) for the clones 100B11 and 115E1 when cellobiose is used as substrate.

Example 3

3rd Round of Shuffling

The sequences of the improved genes obtained in the second round of shuffling were subsequently subjected to a third round of shuffling (still according to the patented method described in EP1104457B1). In order to increase the genetic diversity, at least one gene encoding a beta-glucosidase having 70% identity was added. In this specific example, the gene of the putative glucosidase of *Neurospora crassa* (gene C) (SEQ ID No. 17 and SEQ ID No. 18) and the gene of the putative glucosidase of *Chaetomium globosum* (gene A) (SEQ ID No. 15 and SEQ ID No. 16) were used.

1—High-throughput Screening

A high-throughput screening test as described previously (with the exception of the IPTG induction step, since the improvement provided in the first round of shuffling enables detection of the beta-glucosidase activity based only on the leakage of the promoter) was carried out on the clones obtained following this third round of shuffling, in order to select the best clones, i.e. those having an improvement factor greater than 2 in terms of the beta-glucosidase activity when compared with the clone 115E1.

Under these screening conditions, an improvement in the beta-glucosidase activity compared with the reference enzyme (115E1) was found in particular for the clone 149G7 (SEQ ID Nos. 13 and 14).

2—Determination of the Improvement in the β-glucosidase Activity 2-1/On pNPGlc

In order to determine the relative kcat, the activity of the clone 149G7 was measured by means of the activity test as described previously.

The results show a 2.4-fold improvement in the enzymatic activity of the clone 149G7 compared with the clone 115E1 and a more than 100-fold improvement compared with BGL1.

Example 4

Improved β-glucosidase Activity in the Presence of Glucose

In order to compare the activity of the clones 149G7, 100B11 and 115E1 with BGL1, the activity of these clones was measured by means of the activity test as described previously on pNPGlc in the presence of 60 g/l of glucose in the reaction medium (reaction product).

FIG. 1 shows that the clone 149G7 retains 61% of its activity in the presence of 60 g/l of glucose, whereas the BGL1 reference parental protein retains only 27% of its activity.

Although the present invention has been described above by means of examples of the preferred embodiments thereof, it is understood that it can be modified without departing from the spirit and nature of the invention as defined in the appended claims.

Example 5

Transformation of *T. Reesei* with the Improved Beta-glucosidase Variants

Each gene corresponding to the variants 115E1, 100B11 and 164A2 was cloned into a vector allowing expression in *Trichoderma reesei* with selection with hygromycin. The gene was placed under the control of a strong promoter, cbh1, inducible at the same time as the other cellulases of *T. reesei*.

The transformation of *Trichoderma reesei* was carried out according to the conventional methods known to those skilled in the art (protoplast transformation by calcium shock and selection with 50 µg/ml of hygromycin). The transformants were purified by sporulation and then subcultured twice in selective medium in order to eliminate the unstable clones. The integration of the DNA of interest was then verified by PCR according to the method described by Yu et al., *Fungal Genet. Biol.* (2004); 41(11):973-981.

The PCR-positive clones were then evaluated in terms of cellulase production in flasks. A few spores of each clone were used to inoculate 50 ml of PD broth medium (Difco). The flasks were incubated for 72 h at 30° C. with shaking at 150 rpm. After 72 h, this preculture was used to inoculate, at 30%, a cellulase production medium having the following composition: lactose (20 g/l), Solka floc cellulose (20 g/l), peptone (5 g/l), $KH_2PO_4$ (15 g/l), $(NH_4)_2SO_4$ (5 g/l), $CaCl_2$ (0.6 g/l), $MgSO_4$ (0.6 g/l), $FeSO_4$ (0.005 g/l), $MnSO_4$ (0.0014 g/l), $ZnSO_4$ (0.0014 g/l), $CoCl_2$ (0.0037 g/l), maleic acid (11.6 g/l), Tris (12.1 g/l) and NaOH (2.08 g/l).

The cultures were incubated at 30° C. with shaking at 150 rpm. After 5 days, the cultures were centrifuged and the protein concentration of the supernatant was measured by the Bradford method. The beta-glucosidase activity of the supernatants was measured by hydrolysis of the chromophoric substrate p-nitrophenyl-beta-D-glucoside (pNPG) under the following conditions:

50 mM of citrate buffer at pH 4.8
5 mM of pNPG
10 µl of sample
incubation at 50° C. for 30 min.

The reaction was stopped by adding 100 µl of 2% sodium carbonate. The amount of para-nitrophenol released by hydrolysis of the pNPG was measured by measuring the absorbance at 410 nm and compared with a para-nitrophenol range. The reaction was linear from 25 to 400 µM of para-nitrophenol.

Figure 2:
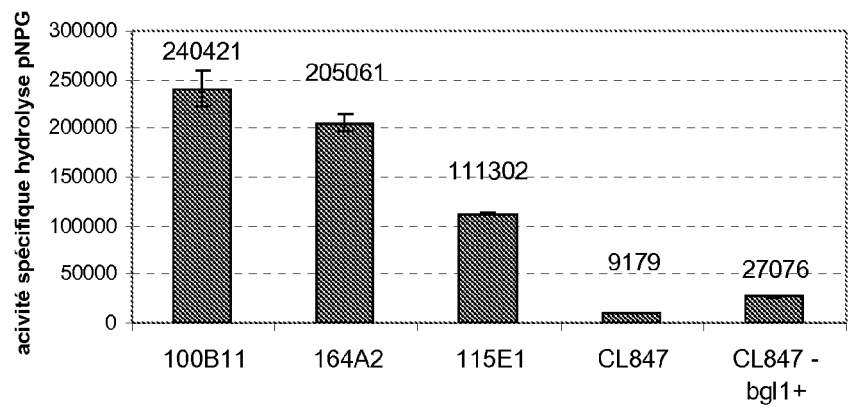
FIG. 2 is a graph representing the specific beta-glucosidase activity of the enzymatic mixtures produced in flasks by the transformed clones (100B11, 164A2 and 115E1) and the starting strain CL847. The CL847-bg11+ strain is indicated by way of comparison.

FIG. 2 shows the results obtained for each variant (one example per variant), in comparison with the activities measured on a nontransformed strain (CL847) and with a strain transformed with the native beta-glucosidase of *T. reesei* (CL847-bgl1+).

Table 6 gives the improvement factors relative to the initial strains CL847 (Durand et al., *Enzyme Microb. Technol.*, 1988; 10:341-346) and CL847-bgl1+, which overexpresses the native beta-glucosidase bgl1 of *T. reesei*.

TABLE 6

Specific beta-glucosidase activity increase factors relative to the reference (data resulting from FIG. 2)

| Clones | Increase factor |
| --- | --- |
| CL847 | — |
| CL847-bgl1+ | 2.9 |
| 100B11 | 26.2 |
| 164A2 | 22.3 |
| 115E1 | 12.1 |

Example 6

Enzymatic Activities of a Composition of Cellulases Produced in a Fermenter by a *T. Reesei* Transformant Expressing an Improved Beta-glucosidase The variant 100B11 of example 5 was used to carry out a production of cellulases in a 2 l fermenter.

The production of cellulases is carried out in a mechanically stirred fermenter. The medium has the following composition: KOH (1.66 g/l), 85% $H_3PO_4$ (2 ml/l), $(NH_4)_2SO_4$ (2.8 g/l), $MgSO_4.7H_2O$ (0.6 g/l), $CaCl_2$ (0.6 g/l), $MnSO_4$ (3.2 mg/l), $ZnSO_4.7H_2O$ (2.8 mg/l), $CoCl_2$ (4.0 mg/l), $FeSO_4.7H_2O$ (10 mg/l), Corn Steep (1.2 g/l), antifoam (0.5 ml/l).

The fermenter containing 1.75 l of mineral medium and 70 g of lactose is sterilized at 120° C. and then inoculated with 0.25 l of a liquid preculture of the *Trichoderma reesei* strain CL847. The medium of the preculture, supplemented with potassium phthalate at 5 g/l in order to control the variations in pH, is identical to that of the fermenter. The fungus is grown in preculture on lactose, at the concentration of 30 g/l. The growth of the inoculum lasts from 2 to 3 days and is carried out between 27 and 30° C. on a shaker table.

After 46 hours of growth, the initial substrate of the fermenter is exhausted and the solution of lactose at 250 g/l is injected continuously at the flow rate of 4.5 ml/h up to 142 hours.

The temperature is regulated at 27° C. during the biomass growth phase, and then at 25° C. until the end of the culture. The pH is regulated at 5 during the growth phase, and then at 4 until the end of the culture by adding an aqueous ammonia solution which provides the nitrogen necessary for the synthesis of the excreted proteins. The dissolved oxygen content is maintained above 15 to 20% by action on the aeration and the shaking.

The production of enzymes is monitored by assaying the extracellular proteins by the Folin method (Lowry, *Biol. Chem.* 1951; 193:265-275), after separation of the mycelium by filtration or centrifugation. The beta-glucosidase activity was measured according to the method described above (see example 5) with the substrate pNPG. The FPase filter paper activity was measured according to the method recommended by Mandels et al., *Biotechnology for Biofuels*, 2009; 2:21. The results are given in table 7.

TABLE 7

| | Strains used for the production | | |
| --- | --- | --- | --- |
| | CL847 | CL847-bgl1+ | 100B11 |
| Specific beta-glucosidase activity (IU/mg) of the cellulolytic mixture produced | 10055 | 45176 | 119677 |
| Specific FPase activity (IU/mg) of the cellulolytic mixture produced | 0.5 | 0.4 | 0.65 |
| Beta-glucosidase activity increase factor relative to the strain CL847 | — | 4.5 | 11.9 |

Example 7

Hydrolytic Efficiency on Pretreated Lignocellulosic Substrate of the Cellulolytic Mixture Produced by a *T. reesei* Transformant Expressing an Improved Beta-glucosidase The cellulolytic mixtures produced by the reference strain CL847 and by the transformant expressing the improved beta-glucosidase, 100B11, resulting from example 6 were used to hydrolyze wheat straw pretreated by vapor explosion under acid conditions. The hydrolyses are carried out in a jacketed Bio-Laffite bioreactor stirred with two stirrers of "ship's anchor" type, under the following experimental conditions:

lignocellulosic substrate diluted to 10% of dry matter
reaction volume 2 l
1M acetate buffer, pH 4.8 (pH tested daily)
temperature 48° C.

The whole is impregnated for 12 h at 300 rpm before the addition of 20 mg/g of dry matter of enzyme and is switched to 500 rpm. Samples are taken at 0 h, 5 h, 24 h, 48 h and 72 h after the addition of the enzymes. The enzymes are inactivated by placing the sample in a boiling water bath for 10 minutes. The sample is then centrifuged and the supernatant is filtered before assaying the glucose by HPLC.

Figure 3:
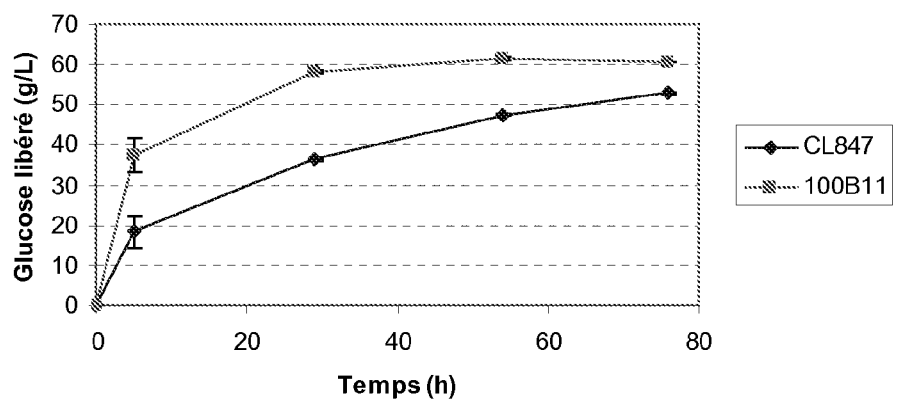
FIG. 3 is a graph representing the results of the hydrolyses (glucose released) for the enzymes produced by the reference strain (CL847) and the variant (100B11).

The results are given in FIG. 3. As early as 24 h, the enzymatic mixture containing the improved beta-glucosidase produced by the transformant 100B11 released twice as much glucose as the enzymatic mixture produced by the reference strain (CL847). The maximum yield is reached as early as 24 h for the mixture resulting from the strain 100B11. At 72 h, this yield has still not been reached for the reference enzymatic mixture (CL847).

The enzymatic mixture produced by the transformant 100B11 therefore has a much greater efficiency than that of the reference enzymatic mixture (CL847) for the same dose of enzyme. This property results in a greater yield and a greater productivity, enabling a more complete hydrolysis of the substrate. Alternatively, it would make it possible to reduce the dose of enzyme to be used in order to obtain an equivalent hydrolysis result. Since the cost of the cellulolytic enzymes represents a large part of the cost price of lignocellulosic bioethanol, any significant reduction in the amount of enzymes to be used can be considered to be a considerable improvement in the method.

The invention claimed is:

1. An isolated or purified modified polypeptide comprising an amino acid sequence in which at least one amino acid is modified compared with the amino acid sequence SEQ ID No. 2, said modified amino acid being chosen from positions 225, 238, 240 and 241 of the amino acid sequence SEQ ID No. 2, wherein said modified polypeptide has the amino acid sequence SEQ ID No. 10; or at least 85% identity with said amino acid sequences SEQ ID No. 2 or SEQ ID NO. 10, and wherein said modified polypeptide has an improved beta-glucosidase activity compared with the beta-glucosidase activity of the wild-type protein having the sequence set forth in SEQ ID No. 2.

2. The modified polypeptide as claimed in claim 1, wherein at least one amino acid of the amino acid sequence is modified compared with the amino acid sequence SEQ ID No. 2, said modification being chosen from Q225H, V238I, T240G and T241S.

3. The modified polypeptide as claimed in claim 1, further comprising at least one additional modified amino acid chosen from positions 97, 99, 100, 118, 119, 121, 123, 126, 127, 128, 130, 132, 134, 135, 140, 147, 151, 153, 163, 168, 173, 174, 177, 179, 182, 187, 193, 206, 207, 212, 217 and 621 of the amino acid sequence SEQ ID No. 2.

4. The modified polypeptide as claimed in claim 1 further comprising at least one additional modified amino acid, said modification being selected from the group consisting of V97I, Y99F, S100G, V118T, N119E, I121M, E123Q, Q126E, F127Y, I128L, E130A, V132A, A134G, S35C, S135V, I140L, P147A, T151I, Q153H, V163T, T168A, G173A, G173S, Q174E, N177E, I179L, V182A, V182N, T187C, L193V, N206D, P207V, L212M, T217L, L621F and L621T.

5. The isolated or purified modified polypeptide as claimed in claim 1, wherein said modified polypeptide has the amino acid sequence SEQ ID No. 10.

6. An enzymatic composition which acts on lignocellulosic biomass, said enzymatic composition being produced by filamentous fungi and comprising at least one modified polypeptide according to claim 1.

7. A method for hydrolyzing a beta-oligosaccharide, comprising contacting a beta-oligosaccharide with a modified polypeptide as claimed in claim 1.

8. A method for hydrolyzing cellobiose to glucose comprising contacting cellobiose with a modified polypeptide as claimed in claim 1.

9. A method for producing biofuel comprising contacting a source of cellulose with a modified polypeptide as claimed in claim 1 to produce glucose and fermenting the glucose to produce a biofuel.

10. A method for producing biofuel from biomass, comprising:
    suspending in an aqueous phase the biomass to be hydrolyzed;
    adding an enzymatic composition which acts on lignocellulosic biomass, as claimed in claim 6, in order to begin the hydrolysis;
    assaying the sugars released;
    separating the sugar solution from the nonhydrolyzed solid fraction;
    fermenting the sugar solution; and
    separating the biofuel from the fermentation must.

11. A method for producing biofuel from biomass, comprising:
    suspending in an aqueous phase the biomass to be hydrolyzed;
    simultaneously adding an enzymatic composition which acts on lignocellulosic biomass, as claimed in claim 6, and a fermentative organism; and
    separating the biofuel from the fermentation must.

* * * * *